(12) United States Patent
Tylkowski et al.

(10) Patent No.: US 10,901,315 B2
(45) Date of Patent: Jan. 26, 2021

(54) PHOTOSENSITIVE MICROCAPSULES

(71) Applicant: Procter & Gamble International Operations SA, Geneva (CH)

(72) Inventors: Bartosz Tylkowski, Tarragona (ES); Anna Trojanowska, Tarragona (ES); Luke Andrew Zannoni, West Chester, OH (US); Marta Giamberini, Tarragona (ES); Calum Macbeath, Singapore (SG); Johan Smets, Bollengerg (BE); Todd Laurence Underiner, Cincinnati, OH (US); Susana FernandezPrieto, Benicarlo Castellon (ES)

(73) Assignee: Procter & Gamble International Operations SA, Geneva (CH)

( * ) Notice: Subject to any disclaimer, the term of this patent is extended or adjusted under 35 U.S.C. 154(b) by 136 days.

(21) Appl. No.: 16/100,239

(22) Filed: Aug. 10, 2018

(65) Prior Publication Data

US 2019/0049838 A1    Feb. 14, 2019

(30) Foreign Application Priority Data

Aug. 11, 2017   (EP) .................................... 17382567

(51) Int. Cl.
  *G03F 7/00*    (2006.01)
  *A01N 25/28*   (2006.01)
  (Continued)

(52) U.S. Cl.
  CPC ............. *G03F 7/002* (2013.01); *A01N 25/28* (2013.01); *A61K 8/11* (2013.01); *A61K 8/91* (2013.01);
  (Continued)

(58) Field of Classification Search
  None
  See application file for complete search history.

(56) References Cited

U.S. PATENT DOCUMENTS 6,348,218 B1   2/2002   Hed et al.
8,957,001 B2   2/2015   Bonnet et al.
(Continued)

FOREIGN PATENT DOCUMENTS

WO   WO2007051198 A2   5/2007
WO   WO2014187833 A1  11/2014
(Continued)

OTHER PUBLICATIONS

Balamurugan et al. "A Visible Light Responsive On-Off Polymeric Photoswitch for the Colorimetric Detection of Nerve Agent Mimics in Solution and in the Vapor Phase", Macromolecules, 2016, 49, pp. 2568-2574.

(Continued)

*Primary Examiner* — Jeffrey D Washville
(74) *Attorney, Agent, or Firm* — James E Oehlenschlager; Jason J Camp

(57) ABSTRACT

A photosensitive microcapsule having a shell encapsulating a core material. The core material can comprise a benefit agent and the shell can comprise a photosensitive polymer. The photosensitive polymer can include one or more photosensitive moieties having a substituted amine and a 1,3 dione moiety. The core material can be released from the photosensitive microcapsule upon exposure to an electromagnetic radiation field selected from the group consisting of infrared radiation, visible light, ultraviolet radiation and mixtures thereof.

15 Claims, 5 Drawing Sheets

(51) Int. Cl.

| | | |
|---|---|---|
| *A61K 9/50* | (2006.01) | |
| *A61Q 13/00* | (2006.01) | |
| *B01J 13/14* | (2006.01) | |
| *C08F 212/08* | (2006.01) | |
| *C08G 73/10* | (2006.01) | |
| *C08L 25/08* | (2006.01) | |
| *C09K 9/02* | (2006.01) | |
| *C11D 1/88* | (2006.01) | |
| *C11D 3/00* | (2006.01) | |
| *G03F 7/037* | (2006.01) | |
| *C08F 222/40* | (2006.01) | |
| *A61K 8/11* | (2006.01) | |
| *C08F 8/00* | (2006.01) | |
| *A61K 8/91* | (2006.01) | |
| *C11D 3/50* | (2006.01) | |
| *C11D 17/00* | (2006.01) | |
| *G03F 7/20* | (2006.01) | |

(52) U.S. Cl.
CPC ............ *A61K 9/5026* (2013.01); *A61Q 13/00* (2013.01); *B01J 13/14* (2013.01); *C08F 8/00* (2013.01); *C08F 212/08* (2013.01); *C08G 73/10* (2013.01); *C08L 25/08* (2013.01); *C09K 9/02* (2013.01); *C11D 1/886* (2013.01); *C11D 3/0063* (2013.01); *C11D 3/505* (2013.01); *C11D 17/0039* (2013.01); *G03F 7/037* (2013.01); *G03F 7/2002* (2013.01); *A61K 2800/412* (2013.01); *A61K 2800/434* (2013.01); *A61K 2800/56* (2013.01); *A61K 2800/81* (2013.01); *C08F 222/404* (2020.02); *C08G 73/1092* (2013.01)

(56) References Cited

U.S. PATENT DOCUMENTS

| | | |
|---|---|---|
| 2004/0121019 A1 | 6/2004 | Perrier et al. |
| 2013/0137625 A1 | 5/2013 | Stowell |
| 2014/0061846 A1 | 3/2014 | Kanematsu et al. |
| 2016/0235685 A1* | 8/2016 | Greaves .................. A61K 8/84 |

FOREIGN PATENT DOCUMENTS

| | | |
|---|---|---|
| WO | WO2014187874 A1 | 11/2014 |
| WO | WO2015044084 A1 | 4/2015 |
| WO | WO2016087948 A2 | 6/2016 |

OTHER PUBLICATIONS

Helmy et al., "Design and Synthesis of Donor-Acceptor Stenhouse Adducts: A Visible Light Photoswitch Derived from Furfural", The Journal of Organic Chemistry, 2014, 79, pp. 11316-11329.

Lerch et al., "Unraveling the Photoswitching Mechanism in Donor-Acceptor Stenhouse Adducts", Journal of the American Chemical Society, 2016, 138, pp. 6344-6347.

Sinawang et al., "Polystyrene Based Visible Light Responsive Polymer with Donor-Acceptor Stenhouse Adduct Pendants", Macromolecular Chemistry and Physics, 2016, 217, pp. 2409-2414.

Sukhdeep et al., "Spatiotemporal Photopatterning on Polycarbonate Surface Through Visible Light Responsive Polymer Bound DASA Compounds", ACS Macro Letters, 2015 American Chemical Society, pp. 1273-1277.

Poelma, et al., "Controlled Drug Release to Cancer Cells from Modular OnePhoton Visible Light-Responsive Micellar System", Chemical Communications, vol. 52, No. 69, dated Aug. 18, 2016, pp. 10525-10528.

Zhong et al., "Polymer dots of DASA-functionalized polyethyleneimine: Synthesis, visible light/pH responsiveness, and their applications as chemosensors", vol. 254, Jul. 2017, pp. 385-392.

* cited by examiner

PHOTOSENSITIVE MICROCAPSULES

The research leading to these results has received co-funding from the People Programme (Marie Curie Actions) of the Seventh Framework Programme of the European Union (FP7/2007-2013) under REA grant agreement no. 600388 (TECNIOspring programme), and from the Agency for Business Competitiveness of the Government of Catalonia, ACCIÓ.

FIELD OF THE INVENTION

The present invention is generally related to microcapsules, more particularly photosensitive microcapsules, compositions comprising such microcapsules, and processes for making and using such microcapsules.

BACKGROUND OF THE INVENTION

Consumer products such as personal care compositions, cleaning compositions and fabric care compositions often include benefit agents. Benefit agents such as perfumes may delight the user by providing a freshness feeling and may serve as a signal to the user that the product may still be working or that the product is still present. However, benefit agents are expensive and may be less effective when employed at high levels in such compositions.

Microcapsules have been used to encapsulate benefit agents in consumer products in order to improve the delivery efficiency of benefit agents. However, current microcapsules release their contents only under certain external stimuli, such as pressure, temperature, or pH, which are not appropriate or advantageous for all applications. For instance, many microcapsules need to be mechanically broken at the desired time to release the benefit agent contained within. In consumer product applications where limited mechanical forces are available (e.g. drapery or upholstery refreshing, shampoos, conditioners, hair sprays, styling gels, hard surface treatment applications, floor cleaners, and dust removing products) the benefit agent may not be released when desired.

As such, there is a need for a microcapsule that can release a benefit agent under less restrictive external stimuli conditions, particularly upon exposure to electromagnetic radiation, preferably visible light.

SUMMARY OF THE INVENTION

A photosensitive microcapsule comprising (a) a core material comprising a benefit agent; and (b) a shell comprising a photosensitive polymer; wherein the photosensitive polymer comprises a photosensitive moiety comprising a structure selected from the group consisting of

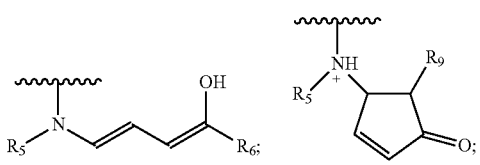

and combinations thereof; wherein $R_5$ is selected from alkyl, substituted alkyl, alkoxy, substituted alkoxy, carboxy, carboxyl, substituted carboxyl, aryl, substituted aryl, or is a carbon atom of a polymer backbone; wherein $R_6$ and $R_9$ comprise a 1,3 dione moiety.

A photosensitive polymer comprising the following structure

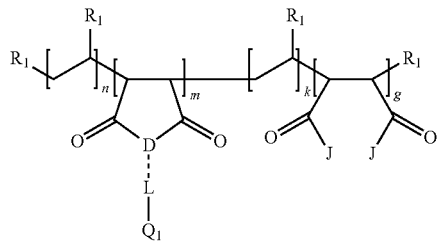

wherein $m+g>0$ and $(n+k)/(m+g) \geq 1$; wherein $R_1$ is selected from H, alkyl, substituted alkyl, alkoxy, substituted alkoxy, aryl, substituted aryl, carboxy, carboxyl, substituted carboxyl, or nitrile; wherein D=N or O; wherein for D=N: L is a linker group containing at least one carbon atom and $Q_1$ is a photosensitive moiety comprising a substituted amine and a 1,3 dione moiety; wherein J=OH, $OR_{12}$, $NH_2$, $NHR_{12}$, or $NR_{12}R_{13}$; wherein $R_{12}$ and $R_{13}$ are independently selected from alkyl, substituted alkyl, alkoxy, aryl, or L-$Q_1$; wherein the photosensitive polymer comprises at least 7 wt % of the photosensitive moiety.

A method of releasing a core material from a photosensitive microcapsule comprising: exposing the photosensitive microcapsule to an electromagnetic radiation field selected from the group consisting of infrared radiation, visible light, ultraviolet radiation and mixtures thereof; wherein the photosensitive microcapsule comprises the core material and a shell; wherein the core material comprises a benefit agent and the shell comprises a photosensitive polymer; wherein the photosensitive polymer comprises a photosensitive moiety comprising the following structure

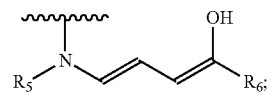

wherein $R_5$ is selected from alkyl, substituted alkyl, alkoxy, substituted alkoxy, carboxy, carboxyl, substituted carboxyl, aryl, substituted aryl, or can be a carbon atom of the photosensitive polymer backbone; wherein $R_6$ is a 1,3 dione moiety.

DETAILED DESCRIPTION OF THE INVENTION

Figure 1:
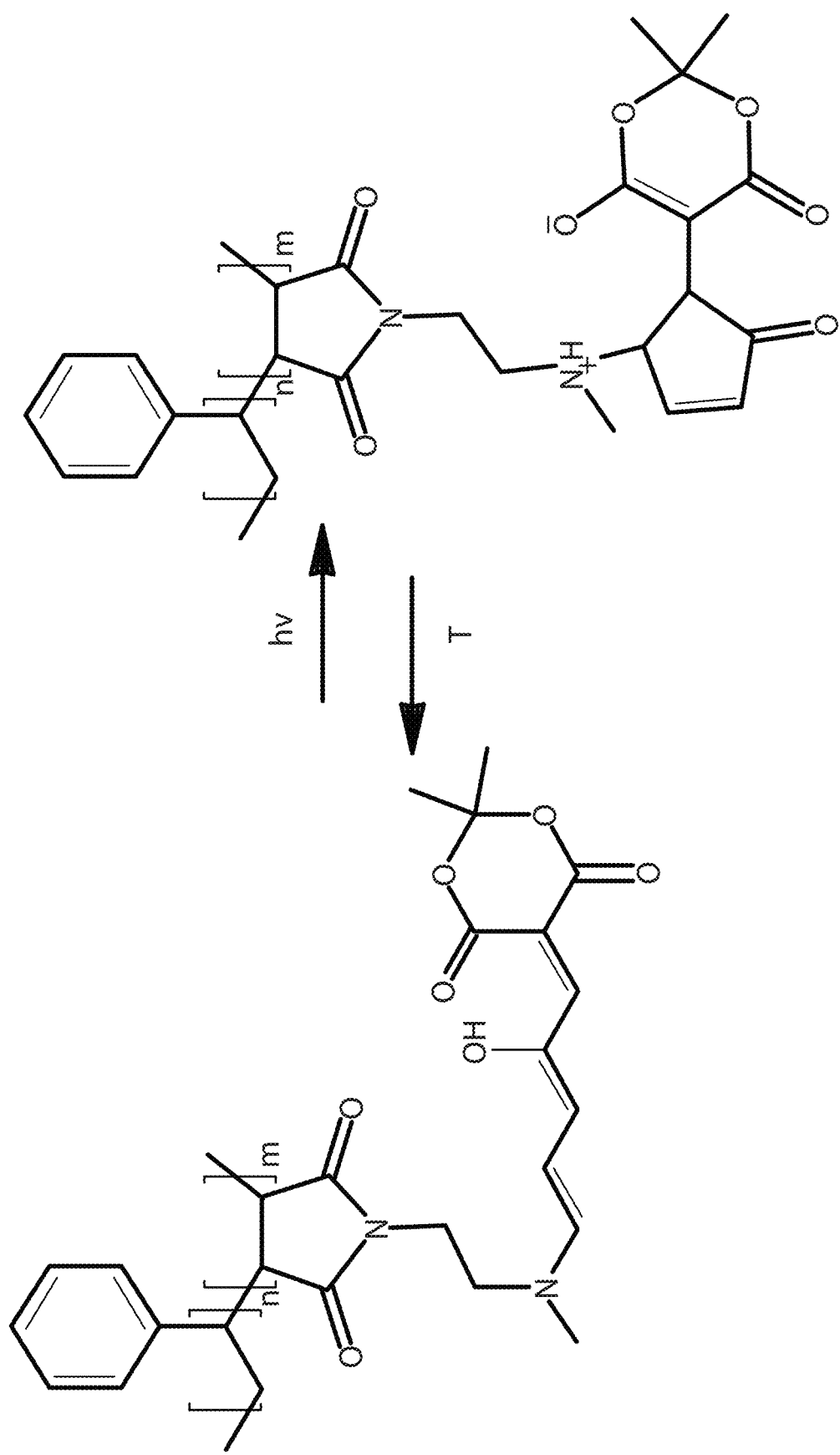
FIG. 1 illustrates the photoisomerization behavior of an exemplary photosensitive polymer comprising a photosensitive moiety upon exposure to visible light.

As used herein, the articles "a" and "an" when used in a claim, are understood to mean one or more of what is claimed or described.

As used herein, "alkyl" refers to straight chained and branched saturated hydrocarbon groups containing 1-30 carbon atoms (i.e., C1-C30), for example, 1-20 carbon atoms (i.e., C1-C20) or 1-10 carbon atoms (i.e., C1-C10). In various embodiments, the alkyl groups of R1, R3-R5 and R7-R8 can be independently selected from C1-C4 alkyls, i.e., alkyl groups having a number of carbon atoms encompassing the entire range (i.e., 1 to about 4 carbon atoms), as well as all subgroups (e.g., 1-2, 1-3, 1-4, 2-3, 2-4, 3-4, 1, 2, 3, and 4 carbon atoms). Non-limiting examples of alkyl groups include allyl, methyl, ethyl, n-propyl, isopropyl, n-butyl, sec-butyl (2-methylpropyl), t-butyl (1,1 dimethylethyl) and propargyl. Unless otherwise indicated, an alkyl group can be an unsubstituted alkyl group or a substituted alkyl group. Alkyl groups optionally can be substituted, for example, with one or more of amino, hydroxy (OH), alkoxy, carboxy, carboxyl, cycloalkyl, heterocycloalkyl, halo, or nitrile.

As used herein, "aryl" refers to any aromatic carbocyclic or heterocyclic group containing unsaturated C—C bonds in conjugation with one another. Examples of "aryl" substituents include, but are not limited to phenyl, napthyl, anthranyl or any aromatic heterocyclic group such as pyridine, pyrazine, indole, purine, furan, thiofuran, pyrrole and the like.

A "substituted" alkyl or aryl refers to an alkyl or aryl having at least one hydrogen radical that is substituted with a non-hydrogen radical (i.e., a substituent). Examples of non-hydrogen radicals (or substituents) include, but are not limited to, alkyl, cycloalkyl, alkenyl, cycloalkenyl, alkynyl, ether, aryl, heteroaryl, heterocycloalkyl, hydroxyl, oxy, alkoxyl, ester, thioester, acyl, carboxyl, cyano, nitro, amino, amido, or sulfur. When a substituted alkyl group includes more than one non-hydrogen radical, the substituents can be bound to the same carbon or two or more different carbon atoms.

As used herein, the term "alkoxy" refers to alkyl-O—, wherein alkyl is defined herein above. An alkoxy group may be branched or unbranched. C1-C6 alkoxy represents, for example: methoxy, ethoxy, propoxy, butoxy, isopropoxy, isobutoxy or tertiary butoxy. Alkoxy includes C3-C6 cycloalkyloxy and C3-C6 cycloalkyl-C1-C6 alkyloxy.

As used herein, "consumer product composition" refers to compositions for treating hair (human, dog, and/or cat), including bleaching, coloring, dyeing, conditioning, growing, removing, retarding growth, shampooing, and styling; deodorants and antiperspirants; personal cleansing; color cosmetics; products relating to treating skin (human, dog, and/or cat), including creams, lotions, ointments, and other topically applied products for consumer use; products relating to orally administered materials for enhancing the appearance of hair, skin, and/or nails (human, dog, and/or cat); shaving; body sprays; fine fragrances such as colognes and perfumes; compositions for treating fabrics, hard surfaces and any other surfaces in the area of fabric and home care, including air care, car care, dishwashing, fabric conditioning (including softening), fabric freshening, laundry detergents, laundry and rinse additive and/or care, hard surface cleaning and/or treatment, and other cleaning for consumer or institutional use; products relating to disposable absorbent and/or non-absorbent articles including adult incontinence garments, bibs, diapers, training pants, infant and toddler care wipes; hand soaps; products relating to oral care including toothpastes, tooth gels, mouth rinses, denture adhesives, and tooth whitening; personal health care medications; wet or dry bath tissue; facial tissue; disposable handkerchiefs; disposable towels and/or wipes; incontinence pads; panty liners; sanitary napkins; tampons and tampon applicators; and combinations thereof.

As used herein, "DASA moiety" refers to a monomer having a donor group comprising a substituted amine and an acceptor group comprising a 1,3 dione moiety.

As used herein, and as understood by one of ordinary skill in the art, a wavy line "⁓" present in certain chemical structures and drawn perpendicular across a bond, e.g.

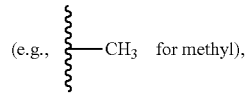

indicates a point of attachment of a chemical group to other parts of an overall molecular or polymeric structure, including to a polymer backbone.

As used herein, "room temperature" refers to a temperature of 23 degrees Celsius (° C.).

All percentages and ratios are calculated by weight unless otherwise indicated. All percentages and ratios are calculated based on the total composition unless otherwise indicated.

Unless otherwise noted, all component or composition levels are in reference to the active portion of that component or composition, and are exclusive of impurities, for example, residual solvents or by-products, which may be present in commercially available sources of such components or compositions.

All weights, measurements and concentrations herein are measured at 23° C. and 50% relative humidity, unless otherwise specified.

Current microcapsules containing benefit agents may not function as desired as such microcapsules may only respond to ineffective and/or undesired external stimuli such as pressure. An alternative approach to pressure-released microcapsules can include photosensitive microcapsules that respond to electromagnetic radiation. A microcapsule having a shell that comprises one or more photosensitive moieties can undergo photoisomerization in response to electromagnetic radiation, permitting the microcapsule to release an encapsulated benefit agent. However, most current photosensitive microcapsules require relatively high energy ultraviolet (UV) light to trigger the photochemical reaction, which can limit their use.

The present invention relates to an improved photosensitive microcapsule comprising a shell having one or more photosensitive moieties which can reversibly switch between two conformational states upon application of electromagnetic radiation, including visible light, allowing for the release of an encapsulated benefit agent under consumer-relevant conditions. Particularly preferred photosensitive moieties comprise Donor-Acceptor Stenhouse Adduct (DASA) moieties.

In one aspect, the present invention relates to a photosensitive microcapsule comprising a core material comprising a benefit agent and a shell comprising a photosensitive polymer. The photosensitive polymer comprises one or more photosensitive moieties that are sensitive to a species of electromagnetic radiation selected from the group consisting of infrared radiation, visible light, UV radiation, and combinations thereof. Upon irradiation, the linear triene extended form of the photosensitive moiety can cyclize to a spatially compact zwitterionic form. The extended form of the photosensitive moiety is hydrophobic and colored while the compact form is hydrophilic and colorless. Without wishing to be bound by theory, it is thought that the absorption of electromagnetic radiation by the photosensitive moiety can cause the photoisomerization of the photosensitive moiety, resulting in a change in morphology of the shell and a corresponding release of the encapsulated core material.

FIG. 1 illustrates the photoisomerization of an exemplary photosensitive polymer comprising a photosensitive moiety before and after irradiation with visible light.

The photosensitive polymer can comprise a photosensitive moiety. The photosensitive moiety can comprise a donor group comprising a substituted amine and an acceptor group comprising a 1,3 dione moiety. Before irradiation, the photosensitive moiety can comprise a substituted amine covalently bound to a first end of a C4 moiety and an oxygen and a 1,3 dione moiety covalently bound to a second end of the C4 moiety. After photoisomerization, the photosensitive moiety can exist as a substituted cyclopent-2-ene-1-one covalently bound to a substituted amine. The photosensitive moiety can be a DASA moiety.

The photosensitive moiety need not comprise a substituted or unsubstituted azobenzene group, a quinine methide group, a nitrobenzyl group, an o-nitrobenzyl group, or a halomethyl-1,3,5-triazine group.

The present invention further relates to a method of releasing a core material from a photosensitive microcapsule comprising exposing the photosensitive microcapsule to an electromagnetic radiation field.

The photosensitive polymer can comprise the structure of Formula Ia

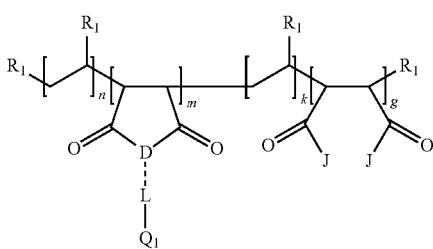

wherein m+g>0 and (n+k)/(m+g)≥1;
wherein $R_1$ is selected from H, alkyl, substituted alkyl, alkoxy, substituted alkoxy, aryl, substituted aryl, carboxy, carboxyl, substituted carboxyl, or nitrile;
wherein D=N or O;
wherein for D=N: L is a linker group containing at least one carbon atom and $Q_1$ is a photosensitive moiety;
wherein J=OH, $OR_{12}$, $NH_2$, $NHR_{12}$, or $NR_{12}R_{13}$;
wherein $R_{12}$ and $R_{13}$ are independently selected from alkyl, substituted alkyl, alkoxy, aryl, or L-$Q_1$.

In one aspect, $R_1$ is an aryl group, as in the case of styrene.

When D=N, the N can be covalently bound to linker group L. Linker group L can be a substituted alkanediyl.

Linker group L can comprise Formula II:

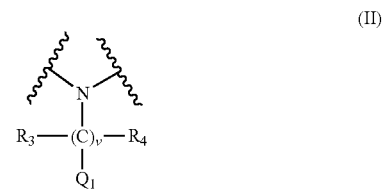

wherein v is an integer from 1-20; and
wherein $R_3$ and $R_4$ can be independently selected from H, alkyl, substituted alkyl, allyl, substituted allyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, alloxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, sulfonyl, substituted sulfonyl, C1-C20 cyclic, substituted C1-C20 cyclic, heterocyclic, and substituted heterocyclic groups.

Representative structures for $R_3$ and $R_4$ are described hereafter.

Alternatively, the photosensitive polymer can comprise the structure of Formula Ib

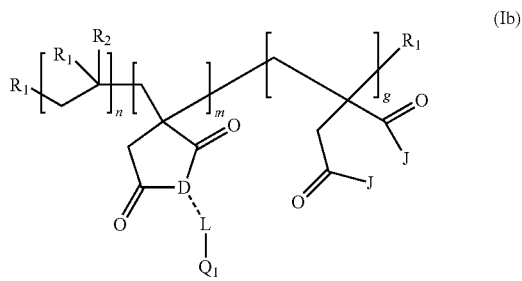

wherein m+g>0 and n≥0;
wherein $R_1$ is selected from H, alkyl, substituted alkyl, alkoxy, substituted alkoxy, aryl, substituted aryl, carboxy, carboxyl, substituted carboxyl, or nitrile;
wherein $R_2$ is selected from H or $CH_3$;
wherein D=N or O;
wherein for D=N: L is a linker group containing at least one carbon atom and $Q_1$ is a photosensitive moiety;
wherein J=OH, $OR_{12}$, $NH_2$, $NHR_{12}$, or $NR_{12}R_{13}$;
wherein $R_{12}$ and $R_{13}$ are independently selected from alkyl, substituted alkyl, alkoxy, aryl, or L-$Q_1$.

Alternatively, the photosensitive polymer can comprise the structure of Formula Ic

wherein b is a repeating monomer unit;
wherein $Z=Q_1$ or $CH_2$;
wherein $A=R_1$ or $A=Q_1$ when $Z=CH_2$;
wherein $Q_1$ is a photosensitive moiety;
wherein $R_1$ is selected from H, alkyl, substituted alkyl, alkoxy, substituted alkoxy, aryl, substituted aryl, carboxy, carboxyl, substituted carboxyl, nitrile, siloxy alkyl, or silo alkyl.

When $Z=Q_1$ the substituted amine can be part of the photosensitive polymer backbone.

The photosensitive polymer can comprise the structure of Formula Id

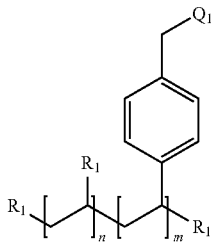

(Id)

wherein m>0 and n≥0;
wherein $R_1$ is selected from H, alkyl, substituted alkyl, alkoxy, substituted alkoxy, aryl, substituted aryl, carboxy, carboxyl, substituted carboxyl, or nitrile;
wherein $Q_1$ is a photosensitive moiety.

Before irradiation, photosensitive moiety $Q_1$ can comprise Formula IIIa:

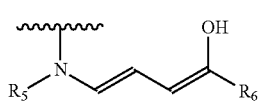

(IIIa)

wherein $R_5$ can be an alkyl, substituted alkyl, alkoxy, substituted alkoxy, carboxy, carboxyl, substituted carboxyl, aryl, substituted aryl, or can be a carbon atom of the photosensitive polymer backbone;
wherein $R_6$ can be a 1,3 dione moiety.

Representative structures for $R_5$ are described hereafter.
$R_6$ can be selected from the group consisting of

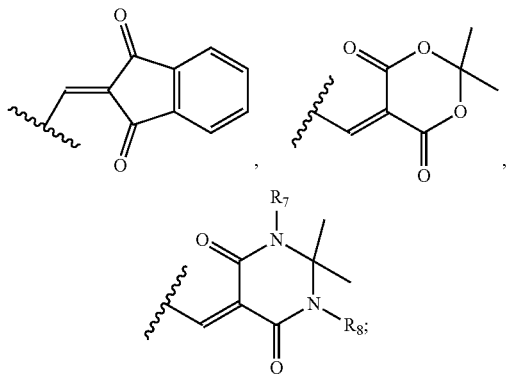

wherein $R_7$ and $R_8$ are independently selected from the group consisting of H, alkyl, substituted alkyl, aryl, or substituted aryl.

After photoisomerization, photosensitive moiety $Q_1$ can comprise Formula IIIb:

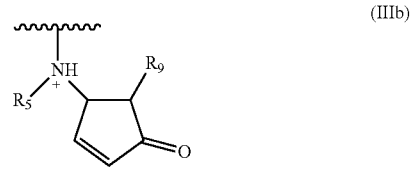

(IIIb)

wherein $R_5$ can be an alkyl, substituted alkyl, alkoxy, substituted alkoxy, carboxy, carboxyl, substituted carboxyl, aryl, substituted aryl, or can be a carbon atom of the photosensitive polymer backbone;
wherein $R_9$ can be a 1,3 dione moiety.

$R_9$ can be selected from the group consisting of

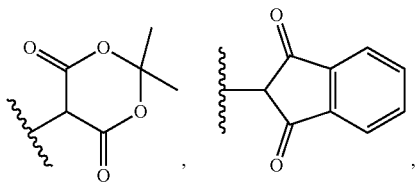

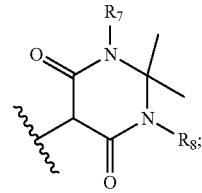

wherein $R_7$ and $R_8$ are independently selected from the group consisting of H, alkyl, substituted alkyl, aryl, or substituted aryl.

Photosensitive moiety $Q_1$ can comprise a formula selected from the group consisting of Formula IIIa, Formula IIIb, and combinations thereof.

Representative structures of $R_3$ and $R_4$ can include, but are not limited to, the following structures:

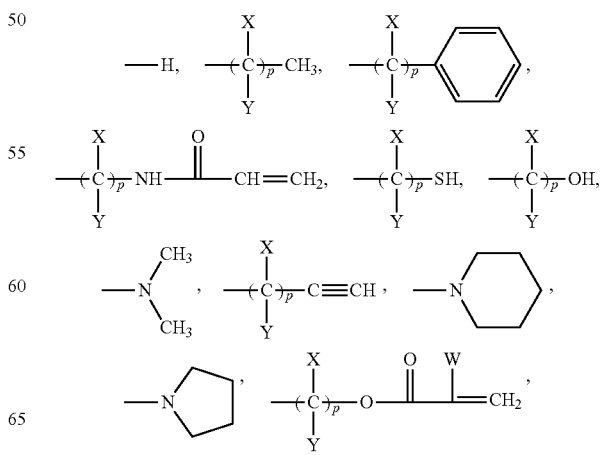

-continued

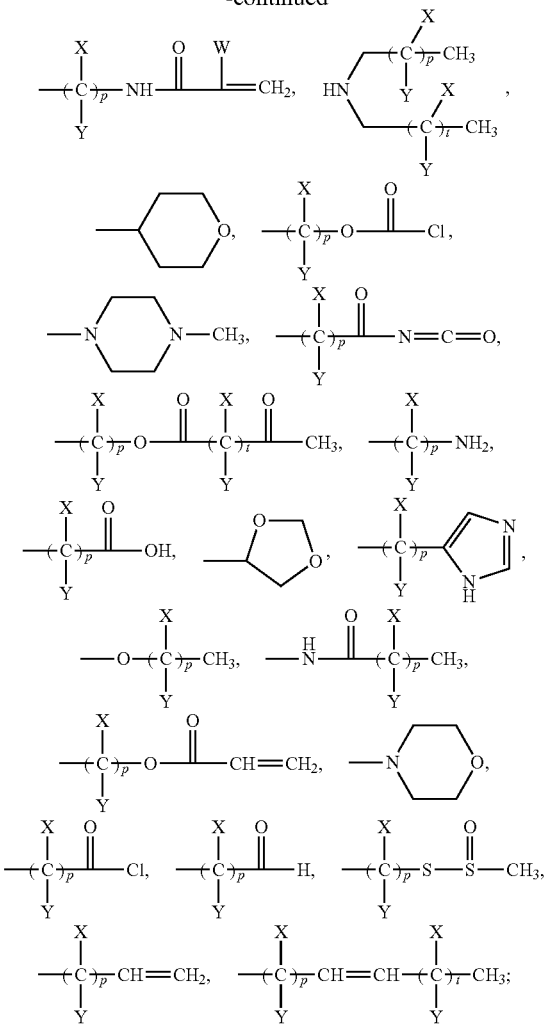

wherein p is an integer from 0 to 20 and t is an integer from 0 to 20;
wherein W, X and Y are independently selected from the group consisting of -continued

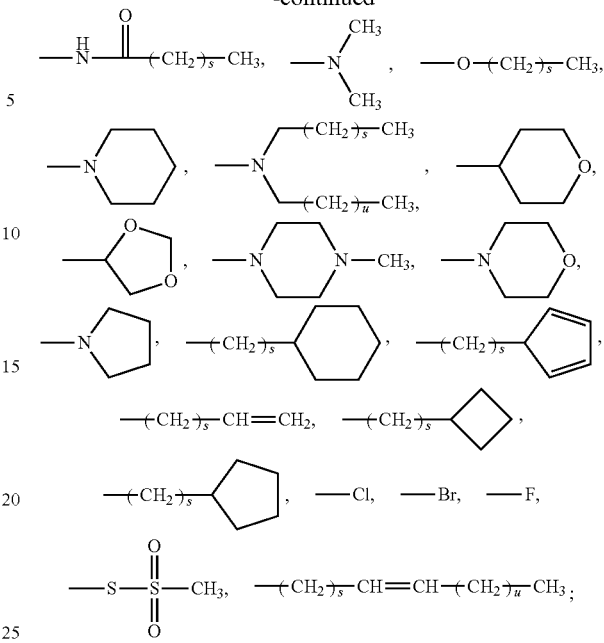

wherein s is an integer from 1 to 20 and u is an integer from 0 to 20.

Representative structures of $R_5$ can include the structures listed above for $R_3$ and $R_4$, excluding H.

A photosensitive polymer can be prepared as described hereafter. First, a starting polymer can undergo a nucleophilic substitution reaction with a diamine comprising a secondary amine to give an amino-functionalized polymer. For example, a starting polymer comprising anhydride or styrene-vinylbenzylchoride can be reacted with a diamine comprising a secondary amine to give an amino-functionalized polymer. Non-limiting examples of starting polymers comprising anhydride or styrene-vinylbenzylchoride can include poly(styrene-co-maleic anhydride), poly(styrene-itaconic anhydride), and poly(styrene-vinylbenzyl chloride). Alternatively, a photosensitive polymer can be prepared without the need for the nucleophilic substitution reaction if the starting polymer is an amino-functionalized polymer comprising a secondary amine in the polymer main chain or the polymer side chain. Non-limiting examples of starting polymers comprising a secondary amine in the polymer main chain or the polymer side chain can include polyethylenimine, silicones comprising secondary amines such as N-ethylaminoisobutyl terminated Poly(dimethylsiloxane) available from Gelest, Inc. (Morrisville, Pa., USA) catalog numbers DMS-A211 and DMS-A214; aminoethylaminopropyl methylsiloxane-dimethyl siloxane copolymers available from Gelest, Inc. (catalog number AMS-233); aminoethylaminoisobutyl methyl siloxane-dimethylsiloxae copolymers available from Gelest, Inc. (catalog number AMS-242); Poly(2-(tert-butylamino)ethyl methacrylate) as a homopolymer or copolymer with (meth)acrylate and (meth)acrylamide comonomers; and Poly(diallyl amine). The secondary amine group of the amino-functionalized polymer can be reacted with a conjugated furfural derivative of Meldrum's acid to form the photosensitive moiety. The conjugated furfural derivative of Meldrum's acid can be formed by condensing furfural with Meldrum's acid.

Non-limiting examples of conjugated furfural derivatives of Meldrum's acid can include 5-((furan-2-yl)methylene)-

2,2-dimethyl-1,3-dioxane-4,6-dione; 5-((furan-2-yl)methylene)-dihydro-1,2,2,3-tetramethylpyrimidine-4,6(1H,5H)-dione; 5-((furan-2-yl)methylene)-2H-indene-1,3-dione; 1,3-dibutyl-5-((furan-2-yl)methylene)-dihydro-2,2-dimethylpyrimidine-4,6(1H,5H)-dione; (E)-5-((furan-2-yl)methylene)-dihydro-2,2,3-trimethyl-1-octylpyrimidine-4,6(1H,5H)-dione; 5-((furan-2-yl)methylene)-dihydro-2,2-dimethyl-1,3-dioctylpyrimidine-4,6(1H,5H)-dione; 5-((furan-2-yl)methylene)-dihydro-2,2-dimethyl-1,3-diphenylpyrimidine-4,6(1H,5H)-dione; 5-((furan-2-yl)methylene)-dihydro-1,3-bis(4-methoxyphenyl)-2,2-dimethylpyrimidine-4,6(1H,5H)-dione; 1,3-bis(4-chlorophenyl)-5-((furan-2-yl)methylene)-dihydro-2,2-dimethylpyrimidine-4,6(1H,5H)-dione; and combinations thereof. Such examples are detailed in Table 1 below.

TABLE 1

Examples of conjugated furfural derivatives of Meldrum's acid

| | |
|---|---|
| 5-((furan-2-yl)methylene)-2,2-dimethyl-1,3-dioxane-4,6-dione | 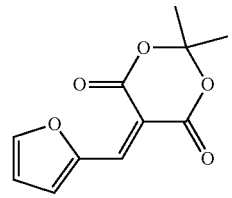 [SMILES: CC1(C)OC(=O)C(=Cc2ccco2)C(=O)O1] |
| 5-((furan-2-yl)methylene)-dihydro-1,2,2,3-tetramethylpyrimidine-4,6(1H,5H)-dione | 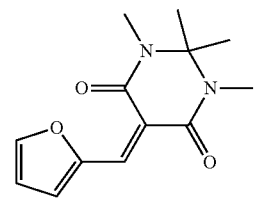 [SMILES: CN1C(=O)C(=Cc2ccco2)C(=O)N(C)C1(C)C] |
| 5-((furan-2-yl)methylene)-2H-indene-1,3-dione | 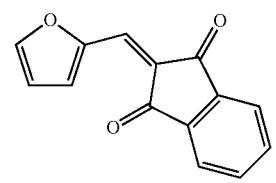 [SMILES: O=C1C(=Cc2ccco2)C(=O)c2ccccc21] |
| 1,3-dibutyl-5-((furan-2-yl)methylene)-dihydro-2,2-dimethylpyrimidine-4,6(1H,5H)-dione | 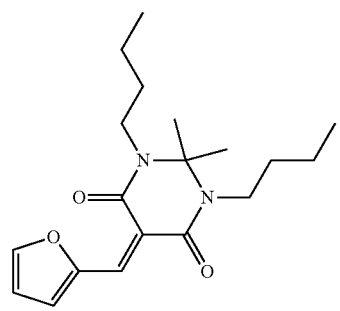 [SMILES: CCCCN1C(=O)C(=Cc2ccco2)C(=O)N(CCCC)C1(C)C] |
| (E)-5-((furan-2-yl)methylene)-dihydro-2,2,3-trimethyl-1-octylpyrimidine-4,6(1H,5H)-dione | 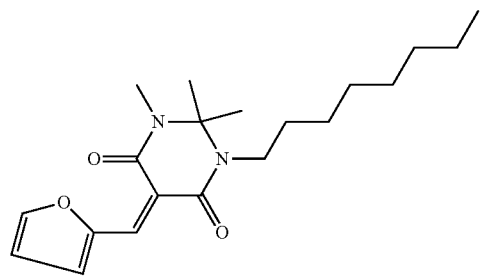 [SMILES: CCCCCCCCN1C(=O)/C(=C/c2ccco2)C(=O)N(C)C1(C)C] |

TABLE 1-continued

Examples of conjugated furfural derivatives of Meldrum's acid 5-((furan-2-yl)methylene)-
dihydro-2,2-dimethyl-1,3-
dioctylpyrimidine-
4,6(1H,5H)-dione

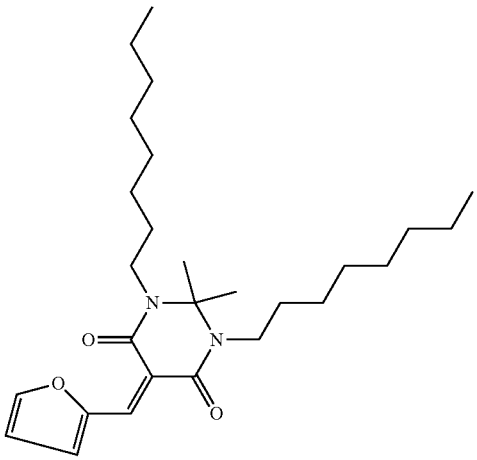 [SMILES: CCCCCCCCN1C(=O)C(=Cc2ccco2)C(=O)N(CCCCCCCC)C1(C)C]

5-((furan-2-yl)methylene)-
dihydro-2,2-dimethyl-1,3-
diphenylpyrimidine-
4,6(1H,5H)-dione

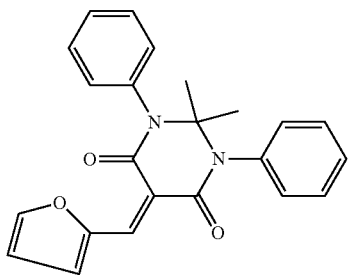 [SMILES: CC1(C)N(c2ccccc2)C(=O)C(=Cc2ccco2)C(=O)N1c1ccccc1]

5-((furan-2-yl)methylene)-
dihydro-1,3-bis(4-
methoxyphenyl)-2,2-
dimethylpyrimidine-
4,6(1H,5H)-dione

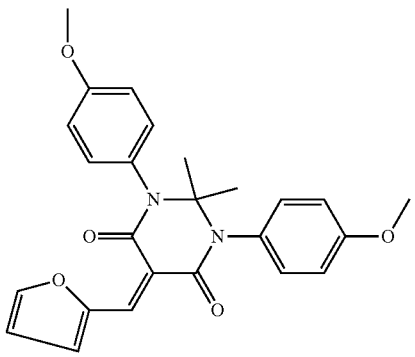 [SMILES: COc1ccc(N2C(=O)C(=Cc3ccco3)C(=O)N(c3ccc(OC)cc3)C2(C)C)cc1]

1,3-bis(4-chlorophenyl)-5-
((furan-2-yl)methylene)-
dihydro-2,2-
dimethylpyrimidine-
4,6(1H,5H)-dione

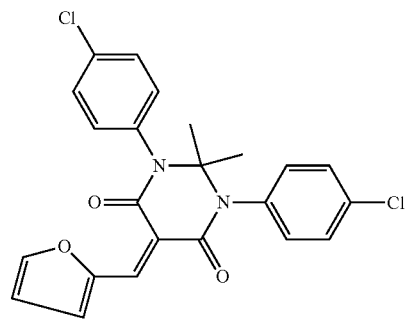 [SMILES: CC1(C)N(c2ccc(Cl)cc2)C(=O)C(=Cc2ccco2)C(=O)N1c1ccc(Cl)cc1]

In one aspect, the shell of the capsule can comprise a mixture of a polymer comprising DASA moiety and a polymer which does not contain DASA moiety.

In one aspect, the shell of the capsule comprising DASA moiety is cross-linked.

In one aspect, the photosensitive moiety (e.g. DASA moiety) can be incorporated in a monomer. Such monomer can then be polymerized to produce a photosensitive polymer. Such monomers comprise at least one secondary amine to react with the DASA photosensitive moiety and at least one reactive group that will enable the polymerization (such as amines, acrylates, acyl chlorides, alcohols, aldehydes, or isocyanates) to form a photosensitive polymer, such as polyureas, polyamides, polyurethanes, polycarbonates, aminoplasts, acrylates, or mixtures thereof.

In one aspect, the monomer that will react with DASA moiety comprises at least one acrylate reactive group and may be selected from:

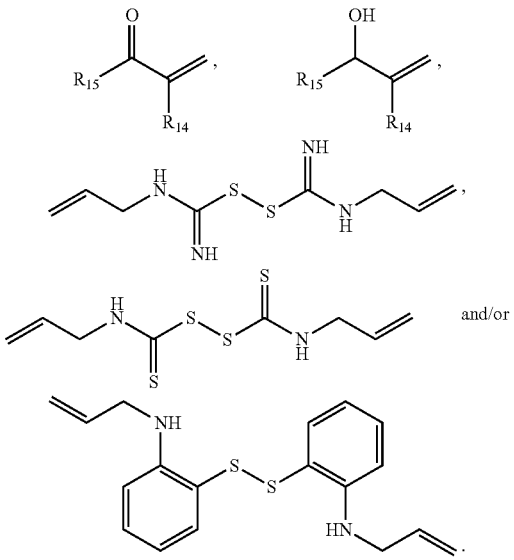

wherein
$R_{14}$ is H or $CH_3$;
$R_{15}$ is selected from the group consisting of

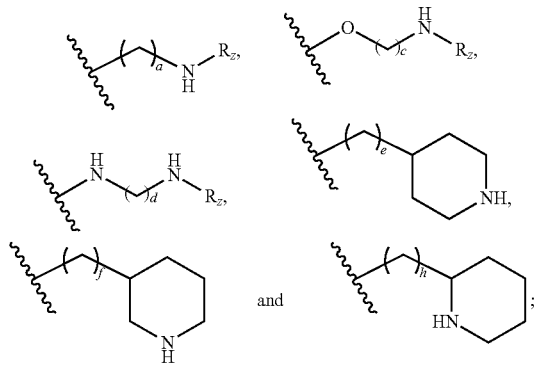

wherein
$R_z$ is selected from the group consisting of

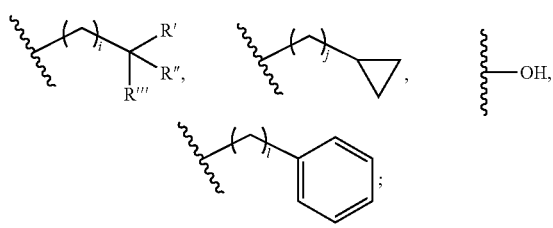

wherein R', R" and R'" are each independently selected from the group consisting of H and $CH_3$;

wherein a, i, j and l are each integers independently selected from 0 to 3; and wherein c, d, e, f and h are each integers independently selected from 1 to 3.

In a preferred aspect, a, c, d, e, f, h, i, j and l are each 2.

In one aspect, the DASA photosensitive monomer may comprise amines as reactive group.

Such DASA-amine monomers and or oligomers may be prepared by the procedure described in Sensors and Actuators B: Chemical, Volume 254, January 2018, Pages 385-392.

In one aspect, the monomer that will react with DASA moiety comprises hydroxyl as reactive group. Such hydroxyl monomers may comprise following structure:

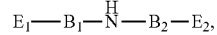

wherein $B_1$ and $B_2$ might be independently selected from:

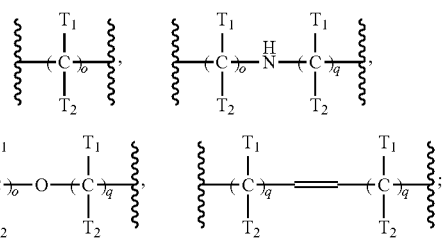

wherein $E_1$ and $E_2$ might be independently selected from the group consisting of:

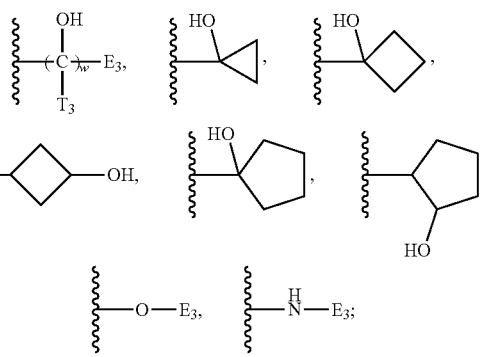

wherein $E_3$ might be selected from:

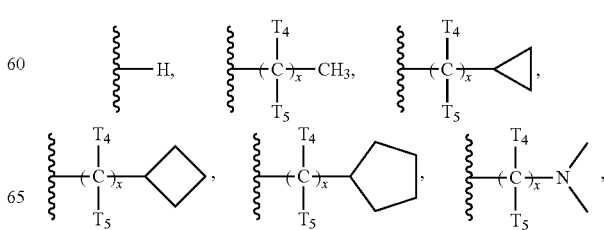

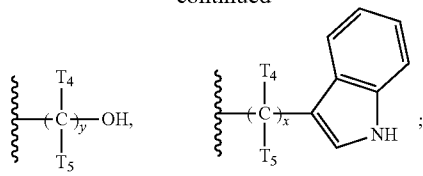 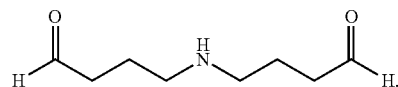

wherein $T_1$, $T_2$, $T_3$, $T_4$ and $T_5$ are independently selected from the group consisting of:

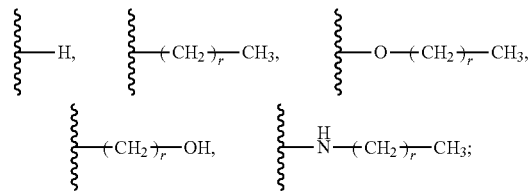

wherein o, q, r, w, x and y are integers. o and y might have values from 1 to 6 and q, r and o might have values from 0 to 6.

In one aspect, the monomer that will react with DASA moiety comprises aldehydes as reactive groups. Non-limiting examples In one aspect, the monomer that will react with DASA moiety comprises carboxylic acids as reactive groups. Non-limiting examples

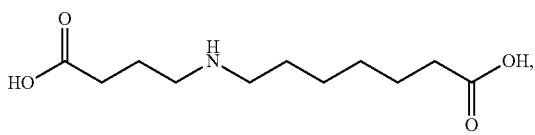

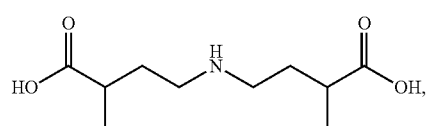

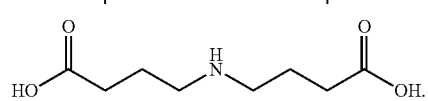

TABLE 2

| | Non-limiting examples of photosensitive monomers: |
|---|---|
| 2-(tert-butyl((1E,3Z)-5-(2,2-dimethyl-4,6-dioxo-1,3-dioxan-5-ylidene)-4-hydroxypenta-1,3-dien-1-yl)amino)ethyl methacrylate | 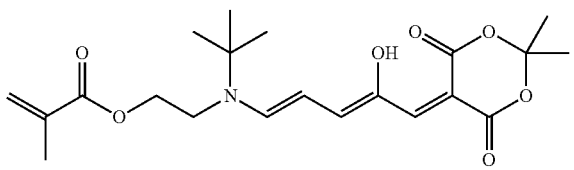 [SMILES: C=C(C)C(=O)OCCN(/C=C/C=C(\O)C=C1C(=O)OC(C)(C)OC1=O)C(C)(C)C] |
| | 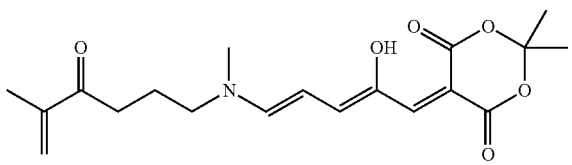 [SMILES: C=C(C)C(=O)CCCN(C)/C=C/C=C(\O)C=C1C(=O)OC(C)(C)OC1=O] |
| 5-((2Z,4E)-2-hydroxy-5-(methyl(3-methyl-2-oxobut-3-en-1-yl)amino)penta-2,4-dien-1-ylidene)-2,2-dimethyl-1,3-dioxane-4,6-dione | 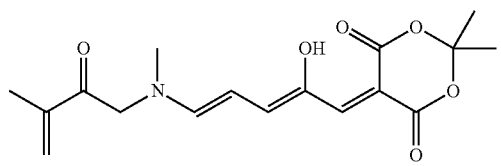 [SMILES: C=C(C)C(=O)CN(C)/C=C/C=C(\O)C=C1C(=O)OC(C)(C)OC1=O] |
| 5-((2Z,4E)-5-(cyclopropyl(4-methyl-3-oxopent-4-en-1-yl)amino)-2-hydroxypenta-2,4-dien-1-ylidene)-2,2-dimethyl-1,3-dioxane-4,6-dione | 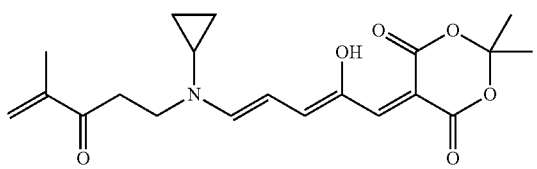 [SMILES: C=C(C)C(=O)CCN(/C=C/C=C(\O)C=C1C(=O)OC(C)(C)OC1=O)C1CC1] |

TABLE 2-continued

Non-limiting examples of photosensitive monomers:

| | |
|---|---|
| 5-((2Z,4E)-2-hydroxy-5-(4-(4-methyl-3-oxopent-4-en-1-yl)piperidin-1-yl)penta-2,4-dien-1-ylidene)-2,2-dimethyl-1,3-dioxane-4,6-dione | 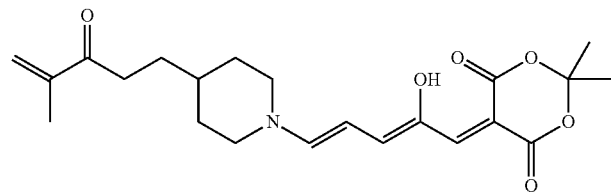 [SMILES: C=C(C)C(=O)CCC1CCN(/C=C/C=C(\O)C=C2C(=O)OC(C)(C)OC2=O)CC1] |
| 2-(tert-butyl((1E,3Z)-4-hydroxy-5-(1,2,2,3-tetramethyl-4,6-dioxotetrahydropyrimidin-5(2H)-ylidene)penta-1,3-dien-1-yl)amino)ethyl methacrylate | 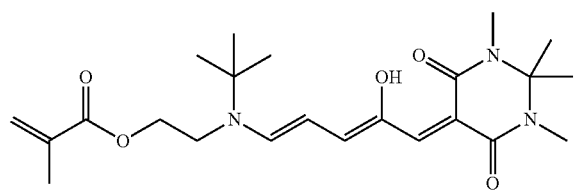 [SMILES: C=C(C)C(=O)OCCN(/C=C/C=C(\O)C=C1C(=O)N(C)C(C)(C)N(C)C1=O)C(C)(C)C] |
| 2-(tert-butyl((1E,3Z)-5-(1,3-dibutyl-2,2-dimethyl-4,6-dioxotetrahydropyrimidin-5(2H)-ylidene)-4-hydroxypenta-1,3-dien-1-yl)amino)ethyl methacrylate. | 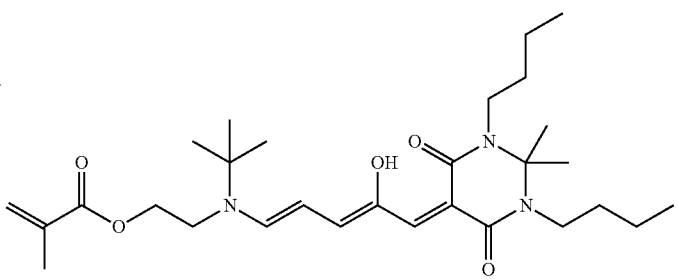 [SMILES: C=C(C)C(=O)OCCN(/C=C/C=C(\O)C=C1C(=O)N(CCCC)C(C)(C)N(CCCC)C1=O)C(C)(C)C] |
| 5-((2Z,4E)-5-((2-ethyl-4-hydroxybutyl)(2-hydroxyethyl)amino)-2-hydroxypenta-2,4-dien-1-ylidene)-2,2-dimethyl-1,3-dioxane-4,6-dione | 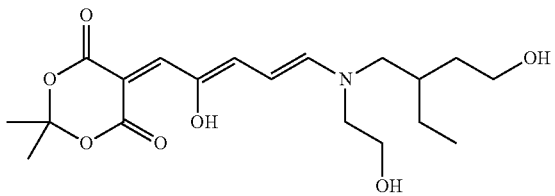 [SMILES: CCC(CCO)CN(/C=C/C=C(\O)C=C1C(=O)OC(C)(C)OC1=O)CCO] |
| 5-((2Z,4E)-5-(bis(2-hydroxyethyl)amino)-2-hydroxypenta-2,4-dien-1-ylidene)-2,2-dimethyl-1,3-dioxane-4,6-dione | 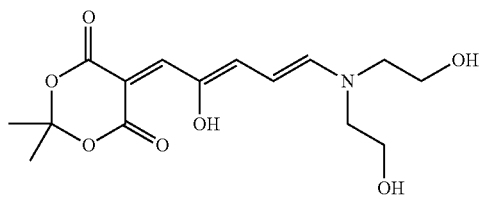 [SMILES: CC1(C)OC(=O)C(=C/C(O)=C/C=C/N(CCO)CCO)C(=O)O1] |
| 4,4'-(((1E,3Z)-5-(2,2-dimethyl-4,6-dioxo-1,3-dioxan-5-ylidene)-4-hydroxypenta-1,3-dien-1-yl)azanediyl)dibutanal | 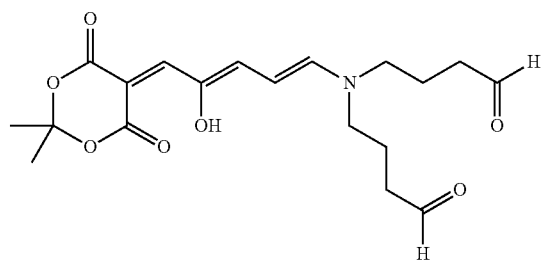 [SMILES: CC1(C)OC(=O)C(=C/C(O)=C/C=C/N(CCCC=O)CCCC=O)C(=O)O1] |

A preferred photosensitive polymer can be synthesized by the route described in Scheme 1. The example shown in Scheme 1 is merely illustrative and is not meant to limit the scope of the invention.

Scheme 1

In step 1, 2,2-dimethyl-1,3-dioxane-4,6-dione is reacted with furfural to provide 5-(furan-2-ylmethylene)-2,2-dimethyl-1,3-dioxane-4,6-dione (IV) by adding 2,2-dimethyl-1,3-dioxane-4,6-dione and furfural to water to form a heterogeneous mixture. The heterogeneous mixture is heated to 75° C. and stirred at that temperature for 2 hours. After the reaction is complete, the mixture is cooled to room temperature. The precipitated solid is collected and washed twice with water. The collected solid is dissolved in trichloromethane and then washed sequentially with saturated aqueous $NaHSO_3$, water, saturated aqueous $NaHCO_3$, and saturated NaCl. The organic layer is dried over $MgSO_4$, filtered, and the solvent is removed. See the procedure reported by Helmy et al. J. Am. Chem. Soc. 2014, 136, 8169.

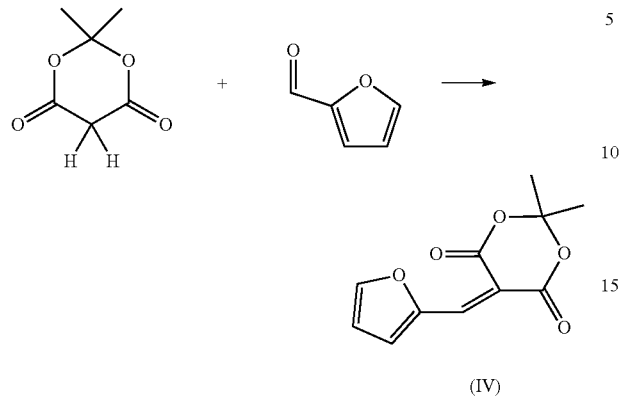

(IV)

In step 2, poly(styrene-co-maleic anhydride) is reacted with n-methyl ethylene diamine to provide poly(styrene-co-maleimide) (V). In particular, poly(styrene-co-maleic anhydride) and dimethylformamide are mixed for 10 minutes at 25° C. Then, a diamine mixture is added dropwise to form a reaction mixture. The reaction mixture is heated to 60° C. and held at that temperature for 2 hours. Next, a strongly acidic ion exchange resin, such as Amberlyst® 15 (available from Sigma-Aldrich, St. Louis, Mo., USA) is added and the reaction is refluxed for 24 hours at 135° C. After reaction completion, the ion exchange resin is filtered off and the filtrate is evaporated under a reduced pressure to yield a solid. The obtained solid is dissolved in tetrahydrofuran and then it is precipitated with n-heptane. See the method described in U.S. Pat. No. 4,812,579.

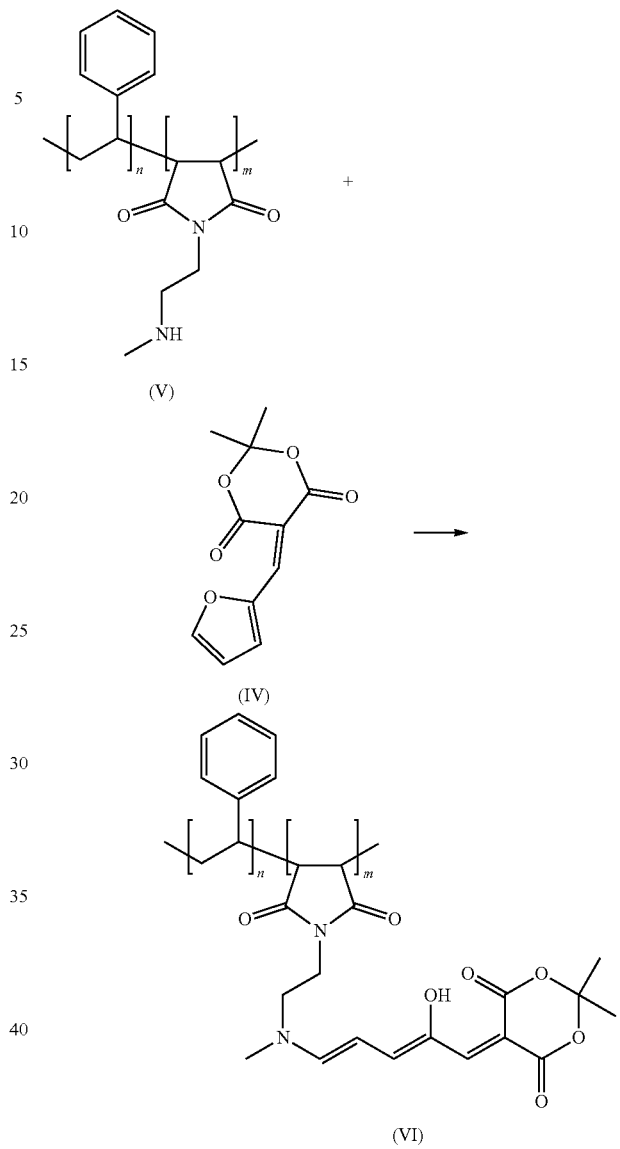

(V)

In step 3, 5-(furan-2-ylmethylene)-2,2-dimethyl-1,3-dioxane-4,6-dione (IV) is reacted with poly(styrene-co-maleimide) (V) to provide poly(styrene-co-maleimide)-5-(furan-2-ylmethylene)-2,2-dimethyl-1,3-dioxane-4,6-dione (VI).

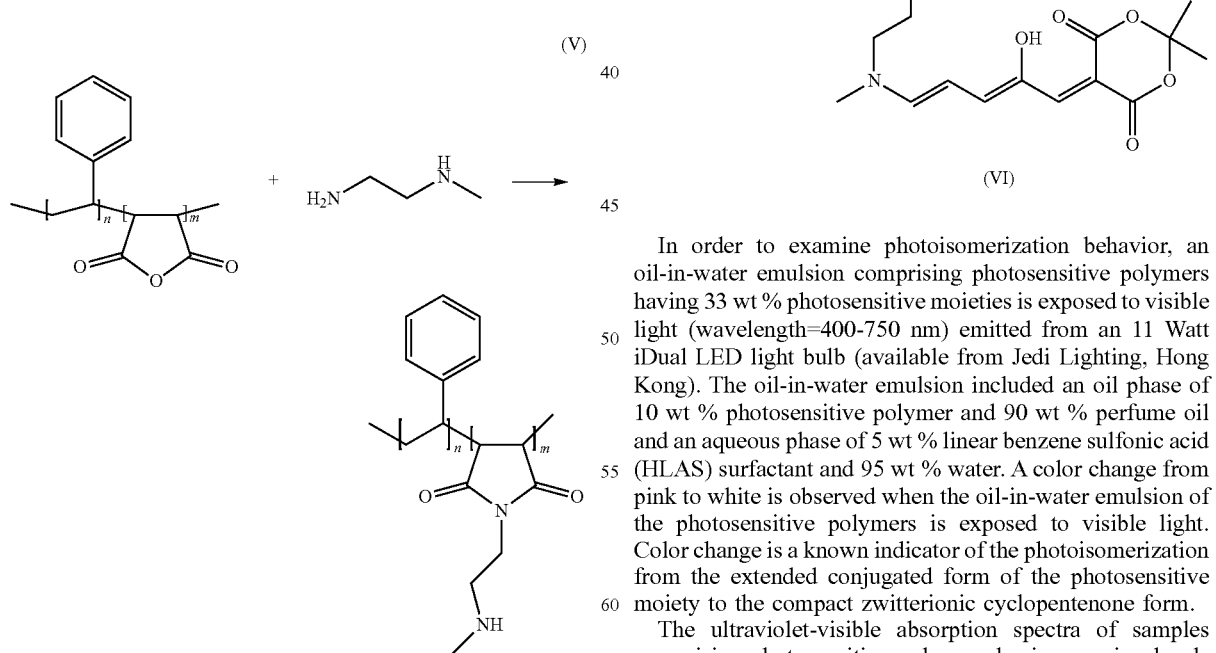

In order to examine photoisomerization behavior, an oil-in-water emulsion comprising photosensitive polymers having 33 wt % photosensitive moieties is exposed to visible light (wavelength=400-750 nm) emitted from an 11 Watt iDual LED light bulb (available from Jedi Lighting, Hong Kong). The oil-in-water emulsion included an oil phase of 10 wt % photosensitive polymer and 90 wt % perfume oil and an aqueous phase of 5 wt % linear benzene sulfonic acid (HLAS) surfactant and 95 wt % water. A color change from pink to white is observed when the oil-in-water emulsion of the photosensitive polymers is exposed to visible light. Color change is a known indicator of the photoisomerization from the extended conjugated form of the photosensitive moiety to the compact zwitterionic cyclopentenone form.

Figure 2:
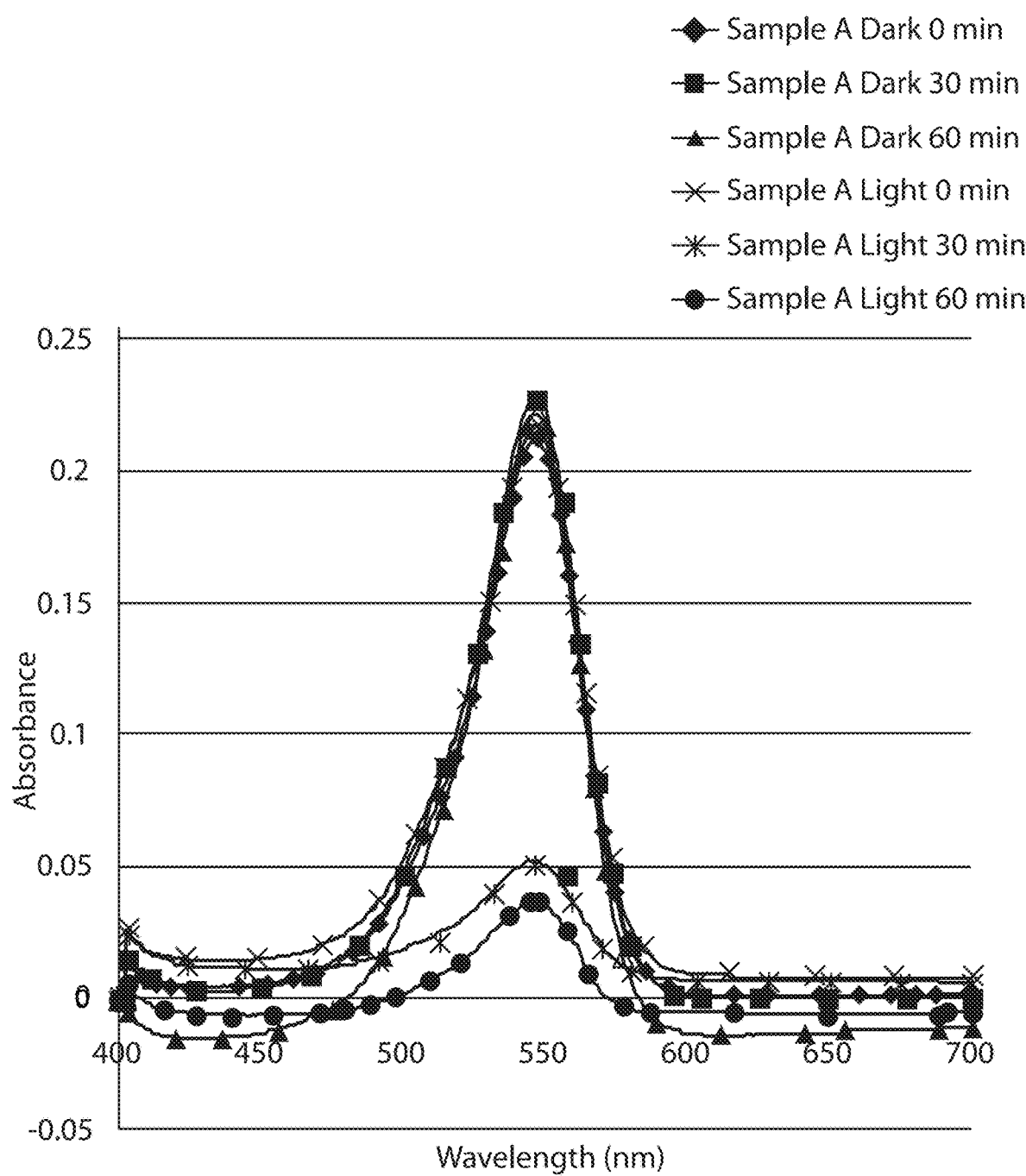
FIG. 2 shows the ultraviolet-visible absorption spectra of a photosensitive polymer comprising 89 wt % polystyrene and 11 wt % photosensitive moiety after irradiation with visible light and a control left in the dark for 0, 30, and 60 minutes.
Figure 3:
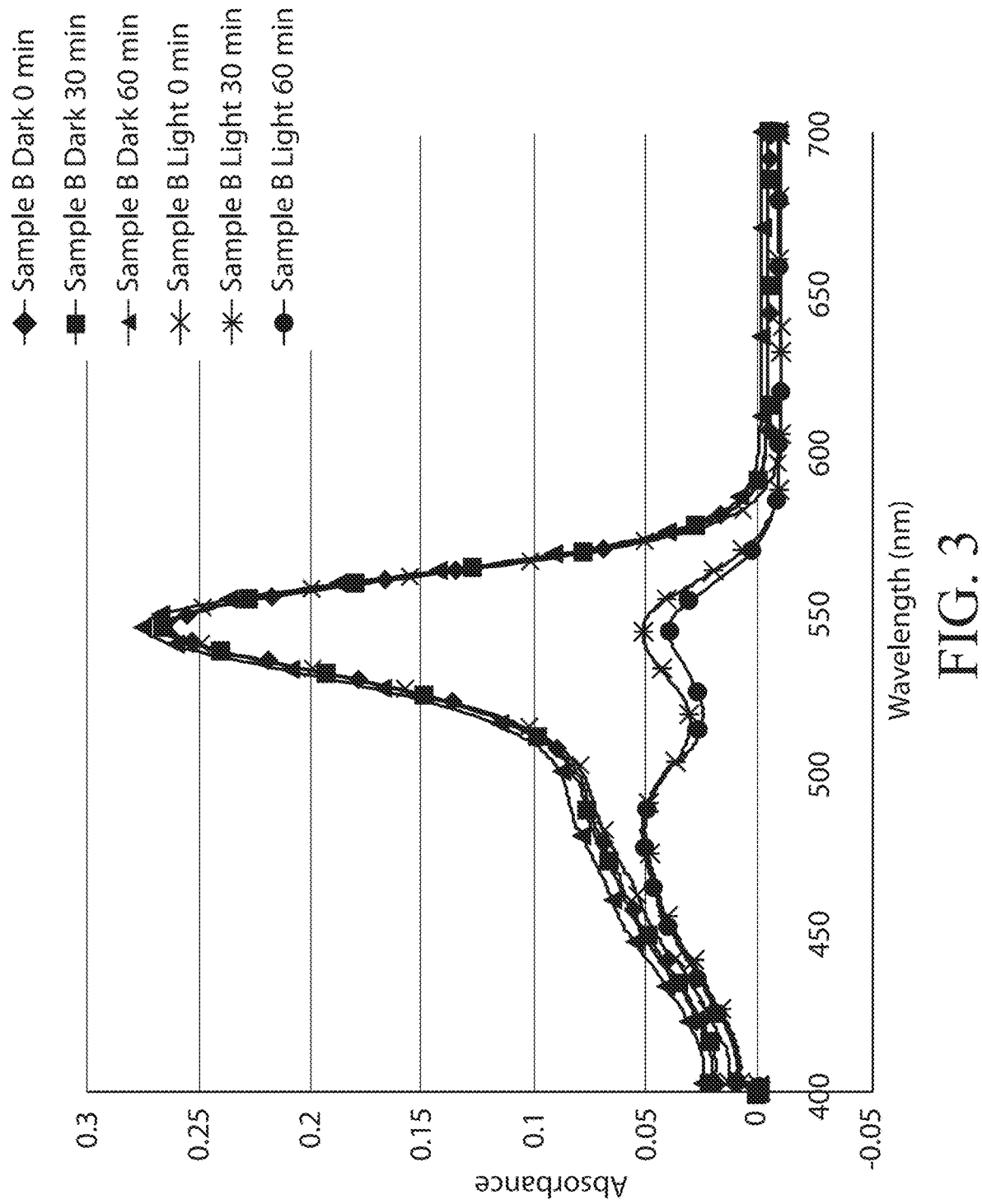
FIG. 3 shows the ultraviolet-visible absorption spectra of a photosensitive polymer comprising 75 wt % polystyrene and 25 wt % photosensitive moiety after irradiation with visible light and a control left in the dark for 0, 30, and 60 minutes.
Figure 4:
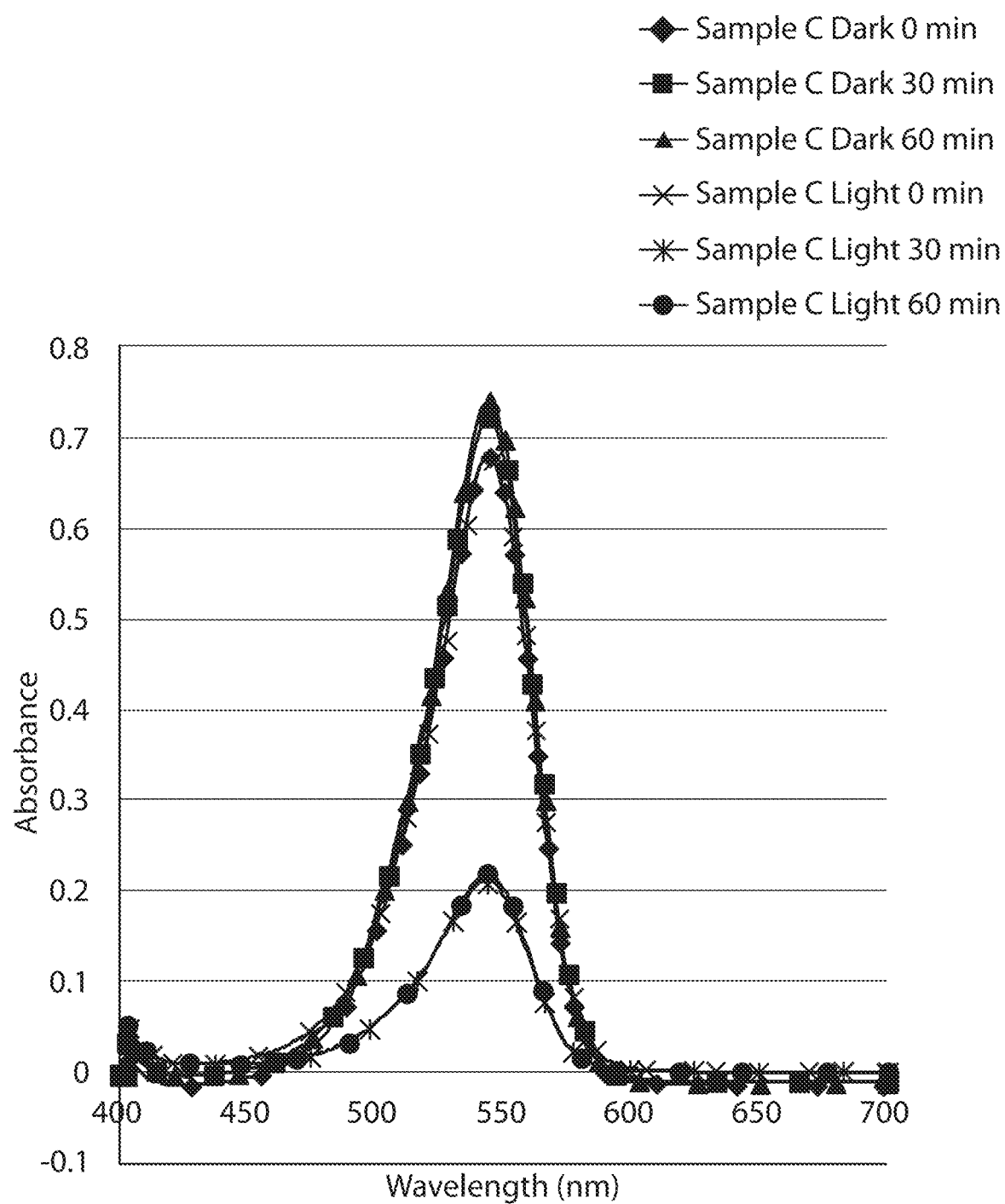
FIG. 4 shows the ultraviolet-visible absorption spectra of a photosensitive polymer comprising 50 wt % polystyrene and 50 wt % photosensitive moiety after irradiation with visible light and a control left in the dark for 0, 30, and 60 minutes.

The ultraviolet-visible absorption spectra of samples comprising photosensitive polymers having varying levels of photosensitive moieties in darkness versus visible light at various time intervals are shown in FIGS. 2-4. FIG. 2 shows the ultraviolet-visible absorption spectra of Sample A comprising a photosensitive polymer of Example 2 (described hereafter), comprising 11 wt % photosensitive moiety, after irradiation with visible light and a control left in the dark for 0, 30, and 60 minutes. FIG. 3 shows the ultraviolet-visible absorption spectra of Sample B comprising a photosensitive polymer of Example 1 (described hereafter), comprising 25 wt % photosensitive moiety, after irradiation with visible light and a control left in the dark for 0, 30, and 60 minutes. FIG. 4 shows the ultraviolet-visible absorption spectra of Sample C comprising a photosensitive polymer of Example 6 (described hereafter), comprising 50 wt % photosensitive moiety, after irradiation with visible light and a control left in the dark for 0, 30, and 60 minutes. Samples A-C are prepared by mixing 0.2 mg of the polymer of Example 2, 1 and 6, respectively, with 0.4 mL of perfume oil. Ultraviolet-visible absorption spectra are measured using a UV-1800 Shimadzu UV Spectrophotometer (available from Shimadzu, Kyoto, Japan).

FIGS. 2-4 show that irradiation with visible light led to a gradual decrease in the absorption band at about 541 nm for Samples A, B and C as compared to control samples left in the dark, suggesting the conversion from the extended to zwitterionic cyclopentenone form of the photosensitive moieties.

In one aspect, the photoisomerization of the photosensitive moieties may be dependent on the level of photosensitive moieties in the photosensitive polymer. In another aspect, the photoisomerization of the photosensitive moieties is not dependent on the level of photosensitive moieties in the photosensitive polymer. Without being limited by theory, it is believed that the more photosensitive moieties in the photosensitive polymer, the slower the photoisomerization may occur because of spatial constraints due to the number of photosensitive moieties present. It is believed that photosensitive polymers having a lower number of photosensitive moieties can undergo photoisomerization faster. Photosensitive polymers comprising higher levels photosensitive moieties may need to be irradiated for longer exposure times to allow for the photoisomerization of the photosensitive moieties.

Microcapsules

Figure 5:
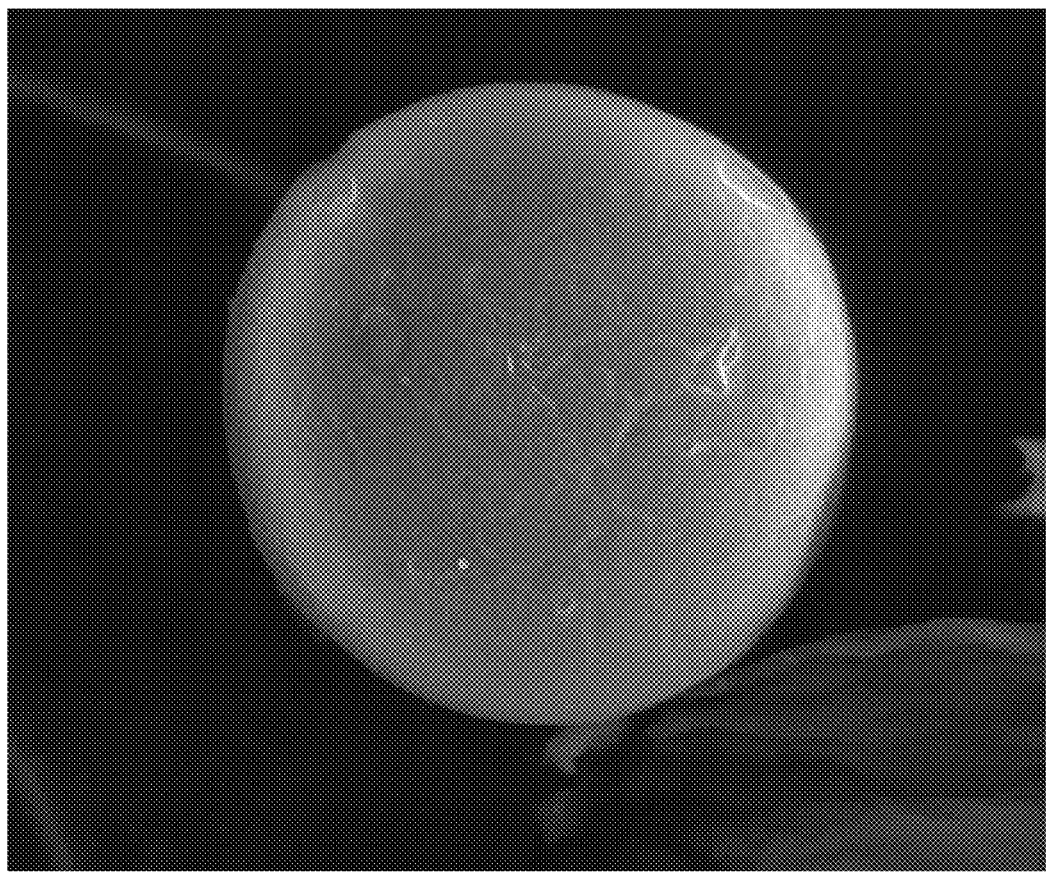
FIG. 5 is a micrograph showing a photosensitive microcapsule comprising a shell comprising a photosensitive polymer comprising 89 wt % polystyrene and 11 wt % photosensitive moiety.

FIG. 5 is a micrograph showing a spherical photosensitive microcapsule comprising a shell comprising a photosensitive polymer encapsulating a core material comprising a perfume. The photosensitive microcapsule is prepared as described hereinafter with 10% w/v of the photosensitive polymer of Example 2 and 90% w/v of perfume oil.

The photosensitive moieties can switch from an extended form to a compact form upon exposure to electromagnetic radiation, thus increasing the porosity of the shell and allowing for the release of the core material. When the electromagnetic radiation is removed from the photosensitive microcapsules, the photosensitive moieties can switch back to the original extended form, thus decreasing the porosity of the shell and inhibiting the release of core material.

The switch from extended form to compact form of the photosensitive moieties can be triggered upon irradiation with electromagnetic radiation selected from the group consisting of infrared radiation, visible light, UV radiation, and combinations thereof. The electromagnetic radiation can have a wavelength of from about 200 nm to about 1000 nm, alternatively from about 300 nm to about 900 nm, alternatively from about 400 nm to about 750 nm, alternatively from about 430 nm to about 650 nm, alternatively from about 480 nm to about 600 nm. Preferably, the electromagnetic radiation comprises a wavelength of about 400 nm to about 750 nm.

It is found that photosensitive moieties undergo faster photoisomerization when exposed to electromagnetic radiation comprising green light (about 480 nm to about 590 nm) as compared to electromagnetic radiation comprising blue light (about 430 nm to about 530 nm), or white light (about 400 nm to about 750 nm). When photosensitive polymers comprising photosensitive moieties are exposed to red light comprising a wavelength of about 500 nm to about 650 nm photoisomerization is not observed.

The photoisomerization behavior of the photosensitive moieties can occur after an exposure time of about 1 minute to about 90 minutes, alternatively about 3 minutes to about 60 minutes, alternatively about 5 minutes to about 45 minutes, alternatively about 10 minutes to about 30 minutes. The photosensitive microcapsules can be exposed to electromagnetic radiation for an exposure time of greater than about 1 minute, alternatively greater than about 3 minutes, alternatively greater than about 10 minutes, alternatively greater than about 30 minutes, alternatively greater than about 60 minutes.

Upon exposure to electromagnetic radiation, from about 1% to about 90% of the core material can be released from the photosensitive microcapsule, alternatively from about 5% to about 75%, alternatively from about 10% to about 60%, alternatively from about 15% to about 50%, alternatively from about 30% to about 40%.

From about 1% to about 90% of the core material can be released from the photosensitive microcapsule within about 1 to about 90 minutes after exposure to electromagnetic radiation, alternatively within about 5 to about 60 minutes, alternatively within about 10 to about 30 minutes. Alternatively, from about 5% to about 75% of the core material can be released from the photosensitive microcapsule within about 1 to about 90 minutes after exposure to electromagnetic radiation, alternatively within about 5 to about 60 minutes, alternatively within about 10 to about 30 minutes. Alternatively, from about 10% to about 60% of the core material can be released from the photosensitive microcapsule within about 1 to about 90 minutes after exposure to electromagnetic radiation, alternatively within about 5 to about 60 minutes, alternatively within about 10 to about 30 minutes. Alternatively, from about 15% to about 50% of the core material can be released from the photosensitive microcapsule within about 1 to about 90 minutes after exposure to electromagnetic radiation, alternatively within about 5 to about 60 minutes, alternatively within about 10 to about 30 minutes.

The photoisomerization behavior of the photosensitive moieties can occur upon exposure to electromagnetic radiation at a temperature range of from about 10° C. to about 50° C. depending on the composition of the encapsulated core material, the environment surrounding the shell, and/or the structure of photosensitive moiety.

The photoisomerization behavior of the photosensitive moieties may depend on the solvent type in which the photosensitive polymer and/or photosensitive microcapsule is dissolved. The photosensitive polymer and/or the photosensitive microcapsule can be dissolved in a solvent, such as toluene, benzene, or xylenes, before exposure to electromagnetic radiation in order for photoisomerization to occur. Alternatively, the photoisomerization behavior of the photosensitive moieties may not depend on the solvent. Without being limited by theory, it is believed that photoisomerization is not solvent dependent when an aromatic group is connected to the amine in the photosensitive moiety. The photosensitive polymer and/or the photosensitive microcapsule need not be dissolved in a solvent before exposure to electromagnetic radiation. The photosensitive polymer and/or the photosensitive microcapsule can be deposited on a dry surface before exposure to electromagnetic radiation.

The photosensitive microcapsules may change color after exposure to electromagnetic radiation. In one aspect the photosensitive microcapsules may change color from pink to white after exposure to electromagnetic radiation due to the conformational change in the photosensitive moieties. Alternatively, the photosensitive microcapsules need not change color after exposure to electromagnetic radiation.

The photosensitive microcapsules can have a diameter of about 10 µm to about 170 µm, alternatively about 30 µm to about 150 µm, alternatively about 45 µm to about 140 µm, alternatively about 60 µm to about 100 µm, alternatively about 75 µm to about 90 µm.

The photosensitive microcapsules can comprise a weight ratio of core material to shell of from about 50:1 to about 1:1, alternatively from about 30:1 to about 1:1, alternatively from about 20:1 to about 1:1, alternatively from about 10:1 to about 1:1, alternatively about 3:1 to about 1:1.

The photosensitive microcapsules can comprise from about 1 wt % to about 25 wt % shell, alternatively from about 5 wt % to about 20 wt %, alternatively from about 8 wt % to about 15 wt %, alternatively from about 10 wt % to about 12 wt %.

The photosensitive microcapsules can comprise from about 75 wt % to about 99 wt % core material, alternatively from about 80 wt % to about 95 wt %, alternatively from about 85 wt % to about 92 wt %, alternatively from about 88 wt % to about 90 wt %.

Shell

The shell can comprise a photosensitive polymer comprising a weight average molecular weight of from about 3,000 g/mol to about 120,000 g/mol, alternatively from about 5,000 g/mol to about 100,000 g/mol, alternatively from about 10,000 g/mol to about 90,000 g/mol.

The shell can comprise a photosensitive polymer comprising any suitable number of photosensitive moieties. The photosensitive polymer can comprise at least one photosensitive moiety. Alternatively, the photosensitive polymer can comprise a plurality of photosensitive moieties. The photosensitive polymer can comprise from about 1 wt % to about 95 wt % photosensitive moiety, alternatively from about 5 wt % to about 80 wt %, alternatively from about 10 wt % to about 50 wt %, alternatively from about 15 wt % to about 40 wt %. This weight percentage can be calculated by dividing the formula mass of the photosensitive moiety by the molar mass of the photosensitive polymer.

The photosensitive polymer can preferably comprise phenyl groups, such as polystyrene as a co-polymeric part of the polymer. The photosensitive polymer can comprise a polystyrene content of from about 40 wt % to about 90 wt %, alternatively about 50 wt % to about 85 wt %, alternatively about 60 wt % to about 75 wt %.

The photosensitive polymer can comprise anhydride and imide. The photosensitive polymer can comprise maleic anhydride and maleimide. Alternatively, the photosensitive polymer can comprise itaconic anhydride and itaconimide. The photosensitive polymer can comprise from about 1 wt % to about 90 wt % anhydride, alternatively about 2 wt % to about 75 wt %, alternatively about 5 wt % to about 50 wt %, alternatively about 10 wt % to about 20 wt %. The photosensitive polymer can comprise from about 1 wt % to about 95 wt % imide, alternatively about 5 wt % to about 80 wt % imide, alternatively about 10 wt % to about 50 wt %, alternatively about 15 wt % to about 40 wt %. One advantage to using a photosensitive polymer comprising anhydride is that the anhydride groups can be cross-linked to form the shell. In one aspect, the shell can comprise a cross-linked photosensitive polymer.

The ratio of polystyrene to anhydride can be from about 1:1 to about 1:10, alternatively about 1:2 to about 1:8, alternatively about 1:3 to about 1:6. The ratio of polystyrene to anhydride can be about 1:1, alternatively about 1:2, alternatively about 1:3, alternatively about 1:4, alternatively about 1:6, alternatively about 1:8.

The shell of the photosensitive microcapsule can be formed when the functional groups of photosensitive polymer are cross-linked. In one aspect the functional groups can comprise anhydride groups, OH, $OR_{12}$, $NH_2$, $NHR_{12}$, $NR_{12}R_{13}$ groups, and combinations thereof. In one aspect, the anhydride groups can be cross-linked with diamines such as 1,8-diaminooctane, 1,10-diaminodecane, 1,7-diaminoheptane, and combinations thereof. The shell can comprise about 1% to about 25%, cross-linked functional groups relative to the total functional group content of the starting polymer used for the photosensitive polymer preparation, alternatively about 2% to about 15%, alternatively about 3% to about 10%. The shell can comprise about 1% to about 3% cross-linked functional groups. Shells comprising cross-linked photosensitive polymers can have a higher stability and can help prevent the photosensitive microcapsules from dissolving in a final product.

The shell can have a thickness of about 5 µm to about 50 µm, alternatively about 10 m to about 35 m, alternatively about 15 m to about 25 m. The shell can have a thickness of about 20 m. The thickness of the shell can be measured at the thickest part of the shell. If the shell is too thin the photosensitive microcapsules may not survive manufacturing and shipping and/or could break and release the benefit agent at an undesirable time before it is exposed to electromagnetic radiation.

Core Material

The encapsulated core material can comprise a benefit agent. Benefit agents can include perfumes, brighteners, biocontrol agents, dyes, silicones, waxes, flavors, vitamins, fabric softening agents, skin care agents, sunscreen agents, enzymes, bleaches, sensates including heating and cooling agents, pharmaceutically active ingredients, and combinations thereof.

Benefit agents useful as core material of the photosensitive microcapsules can be liquid in form at 25° C.

The benefit agent can be hydrophobic. Alternatively, the benefit agent can be hydrophilic. One advantage to having a hydrophilic benefit agent is that when the photosensitive polymer is in the compact, hydrophilic form, a hydrophilic benefit agent can be released faster than a hydrophobic benefit agent.

The benefit agent can comprise one or more perfumes. The one or more perfumes may be selected from any perfume or perfume chemical suitable for topical application to the skin and/or hair, for use in personal care compositions, or for providing freshness to fabrics and/or textiles in fabric care compositions. The perfume may be selected from the group consisting of perfumes, highly volatile perfume materials having a boiling point of less than about 250° C., and mixtures thereof. In one aspect, the perfume is selected from high impact accord perfume ingredients having a C log P of greater than about 2 and odor detection thresholds of less than or equal to 50 parts per billion (ppb).

Non-limiting examples of perfumes can include the perfume raw materials described in Table 3 below.

TABLE 3

Useful Perfume Raw Materials

| Item | Common Name | IUPAC Name |
|---|---|---|
| 1 | Methyl 2-methyl butyrate | methyl 2-methylbutanoate |
| 2 | Isopropyl 2-methyl butyrate | propan-2-yl 2-methylbutanoate |
| 3 | Ethyl-2 Methyl Butyrate | ethyl 2-methylbutanoate |
| 4 | Ethyl-2 Methyl Pentanoate | ethyl 2-methylpentanoate |
| 5 | Ethyl heptanoate | ethyl heptanoate |
| 6 | Ethyl octanoate | Ethyl octanoate |
| 7 | Isobutyl hexanoate | 2-methylpropyl hexanoate |
| 8 | Amyl butyrate | pentyl butanoate |
| 9 | Amyl heptanoate | Pentyl heptanoate |
| 10 | Isoamyl isobutyrate | 3-methylbutyl 2-methylpropanoate |
| 11 | Hexyl acetate | hexyl acetate |
| 12 | Hexyl butyrate | hexyl butanoate |
| 13 | Hexyl isobutyrate | hexyl 2-methylpropanoate |
| 14 | Hexyl isovalerate | hexyl 3-methylbutanoate |
| 15 | Hexyl propionate | hexyl propanoate |
| 16 | Ethyl 2-cyclohexyl propanoate | ethyl 2-cyclohexylpropanoate |
| 17 | Ethyl 3,5,5-trimethyl hexanoate | ethyl 3,5,5-trimethylhexanoate |
| 18 | Glyceryl 5-hydroxydecanoate | 2,3-dihydroxypropyl 5-hydroxydecanoate |
| 19 | Prenyl acetate | 3-methyl 2-butenyl acetate |
| 20 | 3-methyl 2-butenyl acetate | 3-methyl 2-butenyl acetate |
| 21 | Methyl 3-nonenoate | methyl non-3-enoate |
| 22 | Ethyl (E)-dec-4-enoate | Ethyl (E)-dec-4-enoate |
| 23 | Ethyl (E)-oct-2-enoate | Ethyl (E)-oct-2-enoate |
| 24 | Ethyl 2,4-decadienoate | ethyl (2E,4Z)-deca-2,4-dienoate |
| 25 | Ethyl 3-octenoate | ethyl (E)-oct-3-enoate |
| 26 | Citronellyl acetate | 3,7-dimethyloct-6-enyl acetate |
| 27 | Ethyl trans-2-decenoate | ethyl (E)-dec-2-enoate |
| 28 | 2-Hexen-1-yl isovalerate | [(E)-hex-2-enyl] acetate |
| 29 | 2-Hexen-1-yl propionate | [(E)-hex-2-enyl] propanoate |
| 30 | 2-Hexen-1-yl valerate | [(E)-hex-2-enyl] pentanoate |
| 31 | 3-Hexen-1-yl (E)-2-hexenoate | [(Z)-hex-3-enyl] (E)-hex-2-enoate |
| 32 | 3-Hexen-1-yl 2-methyl butyrate | [(Z)-hex-3-enyl] 2-methylbutanoate |
| 33 | 3-Hexen-1-yl acetate | [(Z)-hex-3-enyl] acetate |
| 34 | 3-Hexen-1-yl benzoate | [(Z)-hex-3-enyl] benzoate |
| 35 | 3-Hexen-1-yl formate | [(Z)-hex-3-enyl] formate |
| 36 | 3-Hexen-1-yl tiglate | [(Z)-hex-3-enyl] (Z)-2-methylbut-2-enoate |
| 37 | 2-Methyl butyl 2-methyl butyrate | 2-methylbutyl 2-methylbutanoate |
| 38 | Butyl isovalerate | butyl 3-methylbutanoate |
| 39 | Geranyl acetate | [(2E)-3,7-dimethylocta-2,6-dienyl] acetate |
| 40 | Geranyl butyrate | [(2E)-3,7-dimethylocta-2,6-dienyl] butanoate |
| 41 | Geranyl isovalerate | [(3E)-3,7-dimethylocta-3,6-dienyl] 3-methylbutanoate |
| 42 | Geranyl propionate | [(2E)-3,7-dimethylocta-2,6-dienyl] propanoate |
| 43 | Allyl cyclohexane acetate | prop-2-enyl 2-cyclohexylacetate |
| 44 | Allyl cyclohexyl propionate | prop-2-enyl 3-cyclohexylpropanoate |
| 45 | Allyl cyclohexyl valerate | prop-2-enyl 5-cyclohexylpentanoate |
| 46 | Benzyl octanoate | benzyl octanoate |
| 47 | Cocolactone | 6-pentyl-5,6-dihydropyran-2-one |
| 48 | Coconut decanone | 8-methyl-1-oxaspiro(4.5)decan-2-one |
| 49 | Gamma undecalactone | 5-heptyloxolan-2-one |
| 50 | Gamma-decalactone | 5-hexyloxolan-2-one |
| 51 | Gamma-dodecalactone | 5-octyloxolan-2-one |
| 52 | 37 aphtha lactone | 6-[(E)-pent-2-enyl]oxan-2-one |
| 53 | Jasmolactone | 5-[(Z)-hex-3-enyl]oxolan-2-one |
| 54 | Nonalactone | 6-butyloxan-2-one |
| 55 | 6-acetoxydihydro-theaspirane | [2a,5a(S*)]-2,6,10,10-tetramethyl-1-oxaspiro[4.5]decan-6-yl acetate |
| 56 | Phenoxyethyl isobutyrate | 2-(phenoxy)ethyl 2-methylpropanoate |
| 57 | Pivacyclene | |
| 58 | Verdox | (2-tert-butylcyclohexyl) acetate |
| 59 | Cyclobutanate | 3a,4,5,6,7,7a-hexahydro-4,7-methano-1g-inden-5(or 6)-yl butyrate |
| 60 | Dimethyl anthranilate | methyl 2-methylaminobenzoate |
| 61 | Methyl antranilate | methyl 2-aminobenzoate |
| 62 | Octyl aldehyde | Octanal |
| 63 | Nonanal | Nonanal |
| 64 | Decyl aldehyde | Decanal |
| 65 | Lauric aldehyde | Dodecanal |
| 66 | Methyl nonyl acetaldehyde | 2-methyl undecanal |
| 67 | Methyl octyl acetaldehyde | 2-methyl decanal |
| 68 | 2,4-Hexadienal | (2E,4E)-hexa-2,4-dienal |
| 69 | Intreleven aldehyde | undec-10-enal |
| 70 | Decen-1-al | (E)-dec-2-enal |
| 71 | Nonen-1-al | (E)-2-nonen-1-al |
| 72 | Adoxal | 2,6,10-trimethylundec-9-enal |
| 73 | Geraldehyde | (4Z)-5,9-dimethyldeca-4,8-dienal |
| 74 | Iso cyclo citral | 2,4,6-trimethylcyclohex-3-ene-1-carbaldehyde |
| 75 | d-limonene mainly | 1-methyl-4-prop-1-en-2-yl-cyclohexene |
| 76 | Ligustral | 2,4-dimethylcyclohex-3-ene-1-carbaldehyde |
| 77 | Myrac aldehyde | 4-(4-methylpent-3-enyl)cyclohex-3-ene-1-carbaldehyde |
| 78 | Tridecenal | tridec-2-enal |
| 79 | Triplal | 2,4-dimethyl-3-cyclohexene-1-carboxaldehyde |
| 80 | Vertoliff | 1,2-dimethylcyclohex-3-ene-1-carbaldehyde |
| 81 | Cyclal C | 2,4-dimethylcyclohex-3-ene-1-carbaldehyde |
| 82 | Anisic aldehyde | 4-methoxybenzaldehyde |
| 83 | Helional | 3-(1,3-benzodioxol-5-yl)-2-methylpropanal |
| 84 | Heliotropin | 1,3-benzodioxole-5-carbaldehyde |
| 85 | Neocaspirene | |
| 86 | Beta naphthol ethyl ether | 2-ethoxynaphtalene |
| 87 | Beta naphthol methyl ether | 2-methoxynaphtalene |
| 88 | Hyacinth ether | 2-cyclohexyloxyethylbenzene |
| 89 | 2-heptyl cyclopentanone (fleuramone) | 2-heptylcyclopentan-1-one |
| 90 | Menthone-8-thioacetate | O-[2-[(1S)-4-methyl-2-oxocyclohexyl]propan-2-yl] ethanethioate |
| 91 | Nectaryl | 2-[2-(4-methyl-1-cyclohex-3-enyl)propyl]cyclopentan-1-one |
| 92 | Phenyl Naphthyl Ketone | 38aphthalene-2-yl-phenylmethanone |
| 93 | decen-1-yl cyclopentanone | 2-[(2E)-3,7-dimethylocta-2,6-dienyl] cyclopentan-1-one |
| 94 | fruity cyclopentanone (veloutone) | 2,2,5-trimethyl-5-pentylcyclopentan-1-one |
| 96 | Grapefruit mercaptan | 2-(4-methyl-1-cyclohex-3-enyl)propane-2-thiol |
| 97 | Buccoxime | N-(1,5-dimethyl-8-bicyclo[3.2.1]octanylidene)-hydroxylamine |
| 98 | Labienoxime | 2,4,4,7-Tetramethyl-6,8-nonadiene-3-oneoxime |
| 101 | Diethyl maleate | diethyl but-2-enedioate |
| 102 | Ethyl acetoacetate | ethyl 3-oxobutanoate |
| 103 | Frutonile | 2-Methyldecanenitrile |
| 104 | Methyl dioxolan | ethyl 2-(2-methyl-1,3-dioxolan-2-yl)acetate |
| 105 | Cetalox | 3$^a$,6,6,9$^a$-tetramethyl-2,4,5,5$^a$,7,8,9,9b-octahydro-1H-benzo[e][1]benzofuran |
| 107 | Delta-damascone | (E)-1-(2,6,6-trimethyl-1-cyclohex-3-enyl)but-2-en-1-one |
| 109 | Flor acetate | |
| 110 | Ionone gamma methyl | (E)-3-methyl-4-(2,6,6-trimethyl-1-cyclohex-2-enyl)but-3-en-2-one |
| 113 | Violiff | [(4Z)-1-cyclooct-4-enyl] methyl carbonate |

TABLE 3-continued

Useful Perfume Raw Materials

| Item | Common Name | IUPAC Name |
|---|---|---|
| 114 | Cymal | 3-(4-propan-2-ylphenyl)butanal |
| 115 | Bourgeonal | 3-(4-tert-butylphenyl)propanal |
| 116 | Eucalyptol | 1,3,3-trimethyl-2-oxabicyclo[2,2,2]octane |
| 117 | Freskomenthe | 2-sec-butylcyclohexanone |
| 118 | Gyrane | 2H-Pyran, 6-butyl-3,6-dihydro-2,4-dimethyl- |
| 119 | Alpha-ionone | (E)-4-(2,6,6-trimethyl-1-cyclohex-2-enyl)but-3-en-2-one |
| 120 | Terpinyl acetate | (±)-2-(4-Methyl-3-cyclohexenyl)isopropyl acetate |
| 121 | Melonal | 2,6-Dimethyl-5-heptenal |
| 122 | Aphermate | 1-(3,3-dimethylcyclohexyl)ethyl formate |
| 123 | Dihydro myrcenol | 2,6-dimethyloct-7-en-2-ol |
| 124 | Bacdanol ® | 2-ethyl-4-(2,2,3-trimethyl-3-cyclo-penten-1-yl)-2-buten-1-ol |

Non-limiting examples of biocontrol agents can include biocides, antimicrobials, bactericides, fungicides, algaecides, mildewcides, disinfectants, antiseptics, insecticides, insect and/or moth repellant, vermicides, plant growth hormones, and combinations thereof.

Non-limiting examples of antimicrobials can include comprise glutaraldehyde, cinnamaldehyde, and mixtures thereof.

The core material can optionally further comprise a partitioning modifier. When the core material of the photosensitive microcapsule is an oil such as perfume oil, the properties inherent to the oil may play a role in determining how much, how quickly, and how permeable the shell of the photosensitive microcapsule will be at the oil/water interface. For example, when the oil of the core material comprises highly polar materials, such materials may reduce the diffusion of the monomers and polymers to the oil/water interface, potentially resulting in a relatively thin and highly permeable shell, which can lead to an inferior photosensitive microcapsule. Incorporating a partitioning modifier to adjust the polarity of the core material may alter the partitioning coefficient of the polar materials, allowing for the establishment of a thicker, more stable shell of the photosensitive microcapsule.

Non-limiting examples of partitioning modifiers are described in detail in U.S. Application Publication No. 2011/0268802. Preferred partitioning modifiers are selected from the group consisting of vegetable oil, modified vegetable oil, isopropyl myristate, propan-2-yl tetradecanoate, and mixtures thereof. Suitable vegetable oils are selected from the group consisting of castor oil, soybean oil, and mixtures thereof. Suitable modified vegetable oils are selected from the group consisting of esterified vegetable oil, brominated vegetable oil, and mixtures thereof. Preferred partitioning modifiers are selected from isopropyl myristate, propan-2-yl tetradecanoate, and mixtures thereof.

Consumer Product Composition

The present invention further relates to a consumer product composition comprising one or more photosensitive microcapsules.

The consumer product composition can comprise, based on total composition weight, from about 0.1% to about 25% photosensitive microcapsules, alternatively from about 0.2% to about 15%, alternatively from about 0.4% to about 10%, alternatively from about 1% to about 8%, alternatively from about 3% to about 5%.

The consumer product composition may comprise photosensitive microcapsules and non-photosensitive microcapsules that do not comprise photosensitive moieties. Such non-photosensitive microcapsules may be core-shell microcapsules that can release their core material, which may be a benefit agent such as a perfume, due to the application of a stimuli, including but not limited to, pressure, heat, ionic strength, dehydration and/or diffusion. The benefit agent within non-photosensitive microcapsules may be the same as or different than the benefit agent in the photosensitive microcapsules, depending on the application.

Adjunct Ingredients

The consumer product composition can optionally comprise one or more adjunct ingredients added to the consumer product composition in addition to any encapsulated ingredient. Therefore, the consumer product composition may comprise, for example, a fabric softening agent as an adjunct ingredient and a photosensitive microcapsule comprising a fabric softening agent as a core material.

Non-limiting examples of adjunct ingredients can include: bleaching agents, surfactants, builders, chelating agents, dye transfer inhibiting agents, dispersants, enzymes, enzyme stabilizers, catalytic metal complexes, polymeric dispersing agents, clay and soil removal/anti-redeposition agents, brighteners, suds suppressors, dyes, UV absorbing ingredients, perfumes, structure elasticizing agents, fabric softening agents, conditioning agents, carriers, hydrotropes, processing aids, structurants, anti-dandruff agents, anti-agglomeration agents, pigments and combinations thereof.

The precise nature of the adjunct ingredients, and levels of incorporation thereof, will depend on the physical form of the consumer product composition and the nature of the operation for which it is to be used. However, when one or more adjunct ingredients are present, such one or more adjunct ingredients may be present as detailed below. The following is a non-limiting list of suitable adjunct ingredients.

Surfactants—

The consumer product composition may comprise a surfactant. Suitable surfactants can include the anionic, nonionic, zwitterionic, ampholytic or cationic type or may comprise compatible mixtures of these types. Anionic and nonionic surfactants are typically employed if the composition is a laundry detergent or hair shampoo. In contrast, cationic surfactants are typically employed if the composition is a fabric softener or hair conditioner.

Anionic surfactants suitable for use in the consumer product compositions can include alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference.

Non-limiting examples of anionic surfactants can include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate, and combinations thereof. The anionic surfactant can be sodium lauryl sulfate or sodium laureth sulfate.

The consumer product composition can comprise a nonionic surfactant. The consumer product composition can comprise from about 0.01% to about 30%, alternatively from about 0.01% to about 20%, alternatively from about 0.1% to about 10%, by weight of the composition, of a nonionic surfactant. The nonionic surfactant may comprise an ethoxylated nonionic surfactant. Suitable for use herein are the ethoxylated alcohols and ethoxylated alkyl phenols of the formula $R_{10}(OC_2H_4)_fOH$, wherein $R_{10}$ is selected from the group consisting of aliphatic hydrocarbon radicals containing from about 8 to about 20 carbon atoms and alkyl phenyl radicals in which the alkyl groups contain from about 8 to about 12 carbon atoms, and the average value of f is from about 5 to about 15.

Suitable nonionic surfactants are those of the formula $R_{11}(OC_2H_4)_hOH$, wherein $R_{11}$ is a $C_{10}$-$C_{16}$ alkyl group or a $C_8$-$C_{12}$ alkyl phenyl group, and h is from 3 to about 80. In one aspect, particularly useful materials are condensation products of $C_9$-$C_{15}$ alcohols with from about 5 to about 20 moles of ethylene oxide per mole of alcohol.

The consumer product composition may contain up to about 30%, alternatively from about 0.01% to about 20%, alternatively from about 0.1% to about 20%, by weight of the composition, of a cationic surfactant. Cationic surfactants can include those which can deliver fabric care benefits, non-limiting examples which include: fatty amines, quaternary ammonium surfactants, imidazoline quat materials, and combinations thereof.

Non-limiting examples of cationic surfactants are N,N-bis(stearoyl-oxy-ethyl) N,N-dimethyl ammonium chloride; N,N-bis(tallowoyl-oxy-ethyl) N,N-dimethyl ammonium chloride; N,N-bis(stearoyl-oxy-ethyl); N-(2 hydroxyethyl) N-methyl ammonium methylsulfate; 1,2 di (stearoyl-oxy) 3 trimethyl ammoniumpropane chloride; dialkylenedimethylammonium salts such as dicanoladimethylammonium chloride, di(hard)tallowdimethylammonium chloride, and dicanoladimethylammonium methylsulfate; 1-methyl-1-stearoylamidoethyl-2-stearoylimidazolinium methylsulfate; 1-tallowylamidoethyl-2-tallowylimidazoline; N,N"-dialkyldiethylenetriamine; the reaction product of N-(2-hydroxyethyl)-1,2-ethylenediamine or N-(2-hydroxyisopropyl)-1,2-ethylenediamine with glycolic acid esterified with fatty acid, where the fatty acid is (hydrogenated) tallow fatty acid, palm fatty acid, hydrogenated palm fatty acid, oleic acid, rapeseed fatty acid, or hydrogenated rapeseed fatty acid; polyglycerol esters (PGEs); oily sugar derivatives; wax emulsions; and combinations thereof.

Amphoteric detersive surfactants can include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants can include cocoamphoacetate, cocoamphodiacetate, lauroamphoacetate, lauroamphodiacetate, and mixtures thereof.

Zwitterionic detersive surfactants can include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Alternatively, zitterionic detersive surfactants such as betaines can be selected.

Non-limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678; 2,658,072; 2,438,091; and 2,528,378, which are incorporated herein by reference.

Builders—

The consumer product composition may comprise from about 0.1% to about 80%, by weight of the composition, of a builder. Consumer product compositions in liquid form can contain from about 1% to 10%, by weight of the composition, of the builder. Consumer product compositions in granular form can contain from about 1% to about 50%, by weight of the composition, of the builder.

Detergent builders are well known in the art and can contain, for example, phosphate salts as well as various organic and inorganic nonphosphorus builders. Water-soluble, nonphosphorus organic builders useful herein can include the various alkali metal, ammonium and substituted ammonium polyacetates, carboxylates, polycarboxylates, and polyhydroxy sulfonates. Examples of polyacetate and polycarboxylate builders are the sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid. Other polycarboxylate builders are the oxydisuccinates and ether carboxylate builder compositions comprising a combination of tartrate monosuccinate and tartrate disuccinate. Builders for use in liquid detergents can comprise citric acid. Suitable nonphosphorus, inorganic builders can include silicates, aluminosilicates such as zeolites, borates and carbonates, such as sodium and potassium carbonate, bicarbonate, sesquicarbonate, tetraborate decahydrate, and silicates having a weight ratio of $SiO_2$ to alkali metal oxide of from about 0.5 to about 4.0, or from about 1.0 to about 2.4.

Dispersants—

The consumer product composition may comprise from about 0.1% to about 10%, by weight of the composition, of a dispersant. Dispersants can comprise water-soluble organic materials such as homo- or co-polymeric acids or their salts, in which the polycarboxylic acid may contain at least two carboxyl radicals separated from each other by not more than two carbon atoms. Dispersants may also comprise alkoxylated derivatives of polyamines and/or quaternized derivatives.

Enzymes—

The consumer product composition may comprise one or more enzymes which provide cleaning performance and/or fabric care benefits. Non-limiting examples of suitable enzymes can include hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, and mixtures thereof. A typical combination may be a cocktail of conventional applicable enzymes like protease, lipase, cutinase and/or cellulase in conjunction with amylase. Enzymes can be used at their art-taught levels, for example at levels recommended by suppliers such as Novozymes® (Franklinton, N.C., USA) and Genencor® (Palo Alto, Calif., USA). Typical levels in the consumer product composition can be from about 0.0001% to about 5%, by weight of the composition. When enzymes are present, they can be used at very low levels, e.g., from about 0.001% or lower; or they can be used in heavier-duty laundry detergent formulations at higher levels, e.g., about 0.1% and higher. In accordance with a preference of some consumers for "non-biological" detergents, the compositions may be enzyme-free.

Dye Transfer Inhibiting Agents—

The consumer product composition may comprise a dye transfer inhibiting agent. The consumer product composition can comprise from about 0.0001% to about 10%, by weight of the composition, of one or more dye transfer inhibiting agents, alternatively from about 0.01% to about 2%, alternatively from about 0.05% to about 1%. Non-limiting examples of dye transfer inhibiting agents can include polyvinylpyrrolidone polymers, polyamine N-oxide polymers, copolymers of N-vinylpyrrolidone and N-vinylimidazole, polyvinyloxazolidones, polyvinylimidazoles, and combinations thereof.

Chelants—

The consumer product composition may comprise a chelant. The consumer product composition can comprise less than about 5%, by weight of the composition, of a chelant. Alternatively, the consumer product composition can comprise from about 0.01% to about 3%, by weight of the composition, of a chelant. Non-limiting examples of chelants can include citrates; nitrogen-containing, P-free aminocarboxylates such as ethylenediamine-N,N'-disuccinic acid (EDDS), ethylenediaminetetraacetic acid (EDTA), and diethylenetriaminepentaacetic acid (DTPA); aminophosphonates such as diethylenetriamine pentamethylenephosphonic acid, and ethylenediamine tetramethylenephosphonic acid; nitrogen-free phosphonates e.g., 1-hydroxyethane 1,1-diphosphonic acid (HEDP); nitrogen or oxygen containing, P-free carboxylate-free chelants such as compounds of the general class of certain macrocyclic N-ligands such as those known for use in bleach catalyst systems; and combinations thereof.

Brighteners—

The consumer product composition can comprise a brightener and may comprise any compound that exhibits fluorescence, including compounds that absorb UV light and reemit as "blue" visible light. Non-limiting examples of brighteners can include: derivatives of stilbene or 4,4'-diaminostilbene, biphenyl, five-membered heterocycles such as triazoles, pyrazolines, oxazoles, imidiazoles, etc., or six-membered heterocycles (coumarins, naphthalamide, s-triazine, etc.). Cationic, anionic, nonionic, amphoteric and zwitterionic brighteners can be used. Suitable brighteners include those commercially marketed under the trade name Tinopal-UNPA-GX® by Ciba Specialty Chemicals Corporation (High Point, N.C., USA).

Bleaching Agents—

The consumer product composition may comprise a bleaching agent. Non-limiting examples of bleaching agents can include catalytic metal complexes; activated peroxygen sources; bleach activators; bleach boosters; photobleaches; bleaching enzymes; free radical initiators; $H_2O_2$; hypohalite bleaches; peroxygen sources, including perborate and/or percarbonate; and combinations thereof. Suitable bleach activators can comprise perhydrolyzable esters and perhydrolyzable imides such as, tetraacetyl ethylene diamine, octanoylcaprolactam, benzoyloxybenzenesulphonate, nonanoyloxybenzenesulphonate, benzoylvalerolactam, and dodecanoyloxybenzenesulphonate.

Stabilizers—

The consumer product composition may comprise a stabilizer. Any suitable level of stabilizer may be of use. Exemplary levels of stabilizer can include from about 0.01% to about 20%, from about 0.1% to about 10%, or from about 0.1% to about 3% by weight of the composition. Non-limiting examples of stabilizers can include crystalline, hydroxyl-containing stabilizing agents, trihydroxystearin, hydrogenated oil, or a variation thereof, and combinations thereof. In some aspects, the crystalline, hydroxyl-containing stabilizing agents may be water-insoluble wax-like substances, including fatty acid, fatty ester or fatty soap. In other aspects, the crystalline, hydroxyl-containing stabilizing agents may be derivatives of castor oil, such as hydrogenated castor oil derivatives, for example, castor wax. Other stabilizers can include thickening stabilizers such as gums and other similar polysaccharides, for example gellan gum, carrageenan gum, and other known types of thickeners and rheological additives. Exemplary stabilizers in this class can include gum-type polymers (e.g. xanthan gum); polyvinyl alcohol and derivatives thereof; cellulose and derivatives thereof including cellulose ethers, cellulose esters, and tamarind gum (for example, comprising xyloglucan polymers); guar gum; locust bean gum (in some aspects comprising galactomannan polymers); and other industrial gums and polymers.

Silicones—

The consumer product composition may comprise a second silicone in addition to silicone that may be encapsulated. Therefore, the consumer product composition can comprise a photosensitive microcapsule comprising a silicone as the core material and a second silicone. The second silicone and the silicone of the core material can be the same or can be different.

Suitable silicones comprise Si—O moieties and may be selected from non-functionalized siloxane polymers, functionalized siloxane polymers, and combinations thereof. The molecular weight of the organosilicone is usually indicated by the reference to the viscosity of the material. In one aspect, the organosilicones may comprise a viscosity of from about 10 to about 2,000,000 centistokes at 25° C. In another aspect, suitable organosilicones may have a viscosity of from about 10 to about 800,000 centistokes at 25° C.

Suitable organosilicones may be linear, branched, or cross-linked.

The organosilicone may comprise a cyclic silicone. The cyclic silicone may comprise a cyclomethicone of the formula $[(CH_3)_2SiO]_e$ where e is an integer that may range from about 3 to about 7, or from about 5 to about 6.

The organosilicone may comprise a functionalized siloxane polymer. Functionalized siloxane polymers may comprise one or more functional moieties selected from the group consisting of amino, amido, alkoxy, hydroxy, polyether, carboxy, hydride, mercapto, sulfate phosphate, and/or quaternary ammonium moieties. These moieties may be attached directly to the siloxane backbone through a bivalent alkylene radical, (i.e., "pendant") or may be part of the backbone. Suitable functionalized siloxane polymers include materials selected from the group consisting of aminosilicones, amidosilicones, silicone polyethers, silicone-urethane polymers, quaternary ABn silicones, amino ABn silicones, and combinations thereof.

The functionalized siloxane polymer may comprise a silicone polyether, also referred to as "dimethicone copolyol." In general, silicone polyethers comprise a polydimethylsiloxane backbone with one or more polyoxyalkylene chains. The polyoxyalkylene moieties may be incorporated in the polymer as pendent chains or as terminal blocks. The functionalized siloxane polymer may comprise an amino-silicone.

The organosilicone may comprise amine ABn silicones and quat ABn silicones. Such organosilicones are generally produced by reacting a diamine with an epoxide.

The functionalized siloxane polymer may comprise silicone-urethanes, which are commercially available from Wacker Chemie (Munich, Germany) under the trade name SLM-21200®.

Silicone materials typically serve as conditioning agents in consumer product compositions, such as in fabric softening compositions or hair conditioning compositions.

Perfume—

The consumer product composition may comprise a perfume, which is a neat perfume added to the consumer product composition in addition to any encapsulated perfume. Therefore, the consumer product composition can comprise a neat perfume and a photosensitive microcapsule comprising a perfume as the core material. The neat perfume and the perfume of the core material can be the same or can be different.

Fabric Hueing Agents—

The consumer product composition can comprise a fabric hueing agent. Typically, fabric hueing agents provide a blue or violet shade to fabric. Fabric hueing agents can be used either alone or in combination to create a specific shade of hueing and/or to shade different fabric types. This may be provided, for example, by mixing a red and green-blue dye to yield a blue or violet shade. Fabric hueing agents may be selected from any known chemical class of dye, including but not limited to acridine; anthraquinone (including polycyclic quinones); azine; azo (e.g., monoazo, disazo, trisazo, tetrakisazo, polyazo), including premetallized azo, benzodifurane, and benzodifuranone; carotenoid; coumarin; cyanine; diazahemicyanine; diphenylmethane; formazan; hemicyanine; indigoids; methane; naphthalimides; naphthoquinone; nitro; nitroso; oxazine; phthalocyanine; pyrazoles; stilbene; styryl; triarylmethane; triphenylmethane; xanthenes; and mixtures thereof.

Suitable fabric hueing agents can include dyes, dye-clay conjugates, and organic and inorganic pigments. Suitable dyes can include small molecule dyes and polymeric dyes. Suitable small molecule dyes can be selected from the group consisting of dyes falling into the Colour Index (C.I.) classifications of Acid, Direct, Basic, Reactive or Hydrolysed Reactive, Solvent or Disperse dyes, for example, that are classified as Blue, Violet, Red, Green or Black, and provide the desired shade either alone or in combination. Suitable small molecule dyes can include small molecule dyes selected from the group consisting of Colour Index (Society of Dyers and Colourists, Bradford, UK) numbers Direct Violet dyes such as 9, 35, 48, 51, 66, and 99, Direct Blue dyes such as 1, 71, 80, and 279, Acid Red dyes such as 17, 73, 52, 88, and 150, Acid Violet dyes such as 15, 17, 24, 43, 49, and 50, Acid Blue dyes such as 15, 17, 25, 29, 40, 45, 75, 80, 83, 90, and 113, Acid Black dyes such as 1, Basic Violet dyes such as 1, 3, 4, 10, and 35, Basic Blue dyes such as 3, 16, 22, 47, 66, 75, and 159, Disperse or Solvent dyes as disclosed in U.S. Pat. No. 8,268,016 B2, or dyes as disclosed in U.S. Pat. No. 7,208,459 B2, and mixtures thereof. Suitable small molecule dyes can be selected from the group consisting of C. I. numbers Acid Violet 17, Acid Blue 80, Acid Violet 50, Direct Blue 71, Direct Violet 51, Direct Blue 1, Acid Red 88, Acid Red 150, Acid Blue 29, Acid Blue 113, and mixtures thereof.

Suitable polymeric dyes can include polymeric dyes selected from the group consisting of polymers containing covalently bound (sometimes referred to as conjugated) chromogens, for example polymers with chromogens co-polymerized into the backbone of the polymer and mixtures thereof. Polymeric dyes can include those described in U.S. Pat. No. 7,686,892 B2.

Suitable polymeric dyes can include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In one aspect, suitable polymeric dyes can include polymeric dyes selected from the group consisting of Liquitint® Violet CT, carboxymethyl cellulose (CMC) covalently bound to a reactive blue, reactive violet or reactive red dye such as CMC conjugated with C.I. Reactive Blue 19, sold by Megazyme (Wicklow, Ireland) under the product name AZO-CM-CELLULOSE, product code S-ACMC, alkoxylated triphenyl-methane polymeric colourants, alkoxylated thiophene polymeric colourants, and mixtures thereof.

Suitable dye clay conjugates can include dye clay conjugates selected from the group consisting of at least one cationic/basic dye and a smectite clay, and mixtures thereof. In another aspect, suitable dye clay conjugates can be selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates can include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate, and mixtures thereof.

The fabric hueing agent may be incorporated into the consumer product composition as part of a reaction mixture which is the result of the organic synthesis for a dye molecule, with optional purification step(s). Such reaction mixtures generally comprise the dye molecule itself and in addition may comprise un-reacted starting materials and/or by-products of the organic synthesis route.

Suitable polymeric bluing agents may be alkoxylated. As with all such alkoxylated compounds, the organic synthesis may produce a mixture of molecules having different degrees of alkoxylation. Such mixtures may be used directly to provide the fabric hueing agent, or may undergo a purification step to increase the proportion of the target molecule.

Suitable pigments can be selected from the group consisting of flavanthrone; indanthrone; chlorinated indanthrone containing from 1 to 4 chlorine atoms; pyranthrone; dichloropyranthrone; monobromodichloropyranthrone; dibromodichloropyranthrone; tetrabromopyranthrone; perylene-3,4,9,10-tetracarboxylic acid diimide, wherein the imide groups may be unsubstituted or substituted by $C_1$-$C_3$-alkyl or a phenyl or heterocyclic radical, and wherein the phenyl and heterocyclic radicals may additionally carry substituents which do not confer solubility in water; anthrapyrimidinecarboxylic acid amides; violanthrone; isoviolanthrone; dioxazine pigments; copper phthalocyanine which may contain up to 2 chlorine atoms per molecule; polychloro-copper phthalocyanine or polybromochloro-copper phthalocyanine containing up to 14 bromine atoms per molecule; and mixtures thereof. In another aspect, suitable pigments can be selected from the group consisting of Ultramarine Blue (C.I. Pigment Blue 29), Ultramarine Violet (C.I. Pigment Violet 15), Monastral Blue, and mixtures thereof.

Any mixture of the aforementioned fabric hueing agents can be used according to the needs of the user.

Structurants—

The consumer product composition can comprise a structurant. One advantage to including a structurant is that it can help to suspend the benefit agent. Useful structurants can include polysaccharides, for example, waxy maize or dent corn starch, octenyl succinated starches, derivatized starches such as hydroxyethylated or hydroxypropylated starches, carrageenan, pectin, and mixtures thereof; modified celluloses such as hydrolyzed cellulose acetate, hydroxy propyl cellulose, methyl cellulose, and mixtures thereof; modified proteins such as gelatin; hydrogenated and non-hydrogenated polyalkenes, and mixtures thereof; inorganic salts, for example, magnesium chloride, calcium chloride, calcium formate, magnesium formate, aluminum chloride, potassium permanganate, laponite clay, bentonite clay and mixtures thereof; polysaccharides in combination with inorganic salts; quaternized polymeric materials, for example, polyether amines, alkyl trimethyl ammonium chlorides, diester ditallow ammonium chloride; imidazoles; nonionic polymers with a pKa less than 6.0, for example polyethyleneimine, polyethyleneimine ethoxylate; polyurethanes. Such materials can be obtained from CP Kelco Corp. of San Diego, Calif., USA; Degussa AG of Dusseldorf, Germany; BASF AG of Ludwigshafen, Germany; Rhodia Corp. of Cranbury, N.J., USA; Baker Hughes Corp. of Houston, Tex., USA; Hercules Corp. of Wilmington, Del., USA; and Agrium Inc. of Calgary, Alberta, Canada.

Anti-Agglomeration Agents—

The consumer product composition can comprise an anti-agglomeration agent. Useful anti-agglomeration agents can include divalent salts such as magnesium salts, for example, magnesium chloride, magnesium acetate, magnesium phosphate, magnesium formate, magnesium boride, magnesium titanate, magnesium sulfate heptahydrate; calcium salts, for example, calcium chloride, calcium formate, calcium acetate, calcium bromide; trivalent salts, such as aluminum salts, for example, aluminum sulfate, aluminum phosphate, aluminum chloride hydrate and polymers that have the ability to suspend anionic particles such as suspension polymers, for example, polyethylene imines, alkoxylated polyethylene imines, polyquaternium-6 and polyquaternium-7.

Conditioning Agents—

The consumer product composition can comprise a conditioning agent. Suitable conditioning agents can be selected from the group consisting of silicone material, cationic surfactant, and mixtures thereof. Such materials are described previously herein.

Carriers—

The consumer product composition can be in the form of pourable liquids under ambient conditions. Such compositions will therefore typically comprise a carrier, which can be present at a level of from about 20 wt % to about 95 wt %, or from about 60 wt % to about 85 wt %. The carrier can comprise water, or a miscible mixture of water and organic solvent, and in one aspect may comprise water with minimal or no significant concentrations of organic solvent, except as otherwise incidentally incorporated into the composition as minor ingredients of other components.

Alternatively, the carrier can comprise water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein can include propylene glycol, hexylene glycol, glycerin, and propane diol.

UV-Absorbing Ingredients—

The consumer product composition can comprise a UV-absorbing ingredient. One advantage to including a UV-absorbing ingredient is that it can stabilize the photosensitive microcapsules against premature release of the core material by exposure to light of a sufficient wavelength during storage.

Any suitable UV-absorbing ingredient may be employed, but particularly preferred are those which do not impart an unpleasant color or odor to the composition, and which do not adversely affect the rheology of the product. Non-limiting examples of UV-absorbing ingredients can include avobenzone, cinoxate, ecamsule, menthyl anthranilate, octyl methoxycinnamate, octyl salicylate, oxybenzone, sulisobenzone, and combinations thereof. Other suitable UV-absorbing ingredients are disclosed in U.S. Pat. No. 6,159,918, which is incorporated herein by reference.

UV-absorbing ingredients may not compromise the light-activated performance of the photosensitive microcapsules. Without wishing to be bound by theory, it is believed that in many consumer product applications, e.g., cleaning compositions including laundry detergents, shampoos and body washes, the UV-absorbing ingredient is washed down the drain while the photosensitive microcapsules of the present invention are retained in an efficacious amount on the surface of interest where they are available to release their contents on subsequent exposure to light of a sufficient wavelength. In other cleaning compositions or leave-on consumer products, e.g., floor cleaning compositions, drapery and upholstery refreshers, body lotions, and hair styling products, it is believed that the UV-absorbing ingredients dry down to a thin film after application, allowing the photosensitive microcapsules of the present invention to sit atop or extend above the film. This can allow an efficacious amount of light of the desired wavelength to reach the photosensitive microcapsules and effect the release of the benefit agents.

Packaging Materials

Photosensitive microcapsules and/or consumer product compositions comprising photosensitive microcapsules may be protected against premature release of the core material caused by exposure to light of a sufficient wavelength during storage by judicious selection of packaging. Any suitable package or package material that reduces or eliminates penetration of light into the composition contained therein may be employed. Non-limiting examples of packaging materials can include coated cardboard; fiberboard; paperboard; colored polyolefins including high-density polyethylene (HDPE), low-density polyethylene (LDPE), linear low-density polyethylene (LLDPE) and combinations thereof; polypropylene; coated metal foils; and combinations thereof.

The packaging material can be opaque. Alternatively, the packaging material can be transparent or translucent in order to display the contents contained therein. Non-limiting examples of such transparent or translucent packaging materials can include polyethylene terephthalate (PET), polylactic acid (PLA), polyvinyl chloride (PVC), and blends or multilayer combinations of these materials. In these circumstances, it is understood that an effective means to prevent some wavelengths of light from penetrating through the packaging material, while allowing other wavelengths to pass through, is desirable so that the contents of the package may be seen while still maintaining stability of the embodiments of present invention. Any suitable means to filter or absorb light of the desired wavelength may be employed. A particularly preferred means is to incorporate a UV-absorbing composition into the resin during manufacture of the package, a non-limiting example of which is described in GB 2 228 940, which is incorporated herein by reference. Other means are use of a label or sleeve which absorbs the required wavelength of light.

Method of Use

The photosensitive microcapsules disclosed herein and/or consumer product compositions that contain the photosensitive microcapsules can be used to clean or treat a situs such as a surface, fabric, hair or skin. At least a portion of the situs can be contacted with the photosensitive microcapsules and/or a consumer product composition comprising the photosensitive microcapsules in neat form or diluted in a liquor, such as a wash liquor, and then the situs may be optionally washed and/or rinsed. Alternatively, at least a portion of the situs can be washed and/or rinsed, contacted with the photosensitive microcapsules or a consumer product composition comprising the photosensitive microcapsules, and then optionally washed and/or rinsed again. Washing can include, but is not limited to, scrubbing and mechanical agitation. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

Molecular Weight Test Method

Size-exclusion liquid chromatography (LC) is used to determine the Weight-Average Molecular Weight of the photosensitive polymer. Photosensitive polymer samples (0.1% wt/vol) are dissolved in AcOH/AcNH$_4$ buffer (pH 4.5) and then filtered through a 0.45 µm pore size membrane (available from EMD Millipore, Billerica, Mass., USA). Size-exclusion liquid chromatography (LC) is performed by means of an LC pump (such as the 1260 Infinity pump, Agilent Technologies, Santa Clara, Calif., USA), with two serially-connected columns. Suitable columns can include a model TSK G2500-PW column and a model TSK G6000-PW column, both available from Tosoh Bioscience LLC (King of Prussia, Pa., USA). The detection is achieved via a differential refractometer (such as the model Wyatt Optilab T-rex) coupled on-line with a MALLS detector (such as the model Wyatt Dawn Heleos II) both available from Wyatt Technology Corp. (Santa Barbara, Calif., USA). Degassed AcOH/AcNH$_4$ buffer (pH 4.5) is used as the eluent after two filtrations through 0.22 µm pore size membranes (EMD Millipore). The flow rate is maintained at 0.5 mL/min and the amount of sample injected is 100 µl. Chromatograms are analyzed by software such as the Wyatt Astra version 6.1.2 (Wyatt Technology Corp., Santa Barbara, Calif., USA) to calculate the Weight Average Molecular Weight of the sample.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Example 1 a) Preparation of 5-(furan-2-ylmethylene)-2,2-dimethyl-1,3-dioxane-4,6-dione 1.51 grams (g) of 2,2-dimethyl-1,3-dioxane-4,6-dione and 0.961 g of furfural are added sequentially to 30 mL water to form a heterogeneous mixture. The heterogeneous mixture is heated to 75° C. and stirred at that temperature for 2 hours. During the course of the reaction, a dark green precipitate is formed. At the completion of the reaction (as monitored by thin-layer chromatography using 3:1 hexane:ethyl acetate) the mixture is cooled to room temperature. The precipitated solid is collected by vacuum filtration and is washed twice with 30 mL cold water. The collected solid is dissolved in trichloromethane and washed sequentially with 30 mL saturated aqueous NaHSO$_3$, 30 mL water, 30 mL saturated aqueous NaHCO$_3$, and 30 mL saturated NaCl. The organic layer is dried over MgSO$_4$, filtered, and the solvent is removed by rotary evaporation to give 2.19 g (99%) of 5-(furan-2-ylmethylene)-2,2-dimethyl-1,3-dioxane-4,6-dione as a bright yellow powder.

b) Preparation of a Photosensitive Polymer Containing 75% Polystyrene and 25% maleimide-5-(furan-2-ylmethylene)-2,2-dimethyl-1,3-dioxane-4,6-dione Moieties 5 g of poly(styrene-co-maleic anhydride) 75:25 (available from Total Petrochemicals & Refining USA, Inc., Houston, Tex., USA) and 80 mL of dimethylformamide are placed into a 250 mL round-bottom flask equipped with a reflux condenser with a water-separator, a thermometer, a stirrer, and a dropping funnel. The prepared mixture is stirred for 10 minutes at 25° C. Next, 3.3 mL of a diamine mixture (0.91 g of N-methylethylenediamine and 2.3 mL of dimethylformamide) is added dropwise to form a reaction mixture. Then the reaction mixture is heated to 60° C. and held at that temperature for 2 hours. Next, 0.987 g of a strongly acidic ion exchange resin is added and the reaction is refluxed for 24 hours at 135° C. A suitable strongly acidic ion exchange resin is Amberlyst® 15 (available from Sigma-Aldrich, St. Louis, Mo., USA). After reaction completion, the ion exchange resin is filtered off and the filtrate is evaporated under a reduced pressure to yield a solid. The obtained solid is purified by precipitation. First, it is dissolved in 40 mL of tetrahydrofuran and then it is precipitated with 400 mL of n-heptane.

Then 5 g of the dry precipitate (poly(styrene-co-maleimide)) and 75 mL of tetrahydrofuran are placed into a 250 mL round-bottom flask equipped with a reflux condenser, a thermometer, a stirrer, and an oil bath. Then a solution of 2.39 g of 5-(furan-2-ylmethylene)-2,2-dimethyl-1,3-dioxane-4,6-dione and 40 mL tetrahydrofuran is added. The mixture is heated to 60° C. and kept for 30 minutes at 60° C. to complete the reaction. Next the photosensitive polymer is precipitated from the reaction solution with 1 L of n-heptane, filtrated, and washed with 100 mL of cold diethyl ether. Finally, the photosensitive polymer is dried in a vacuum at 25° C. for 24 hours.

c) Preparation of Photosensitive Microcapsules

Photosensitive microcapsules are prepared in the dark or in red light conditions. Photosensitive microcapsules are obtained by using a nozzle device working in a semi-continuous process with a nozzle size of 70-80 µm. A suitable nozzle is available from Spraying Systems Co. Wheaton, Ill. (dispersion combination type SUF1). The nozzle is connected to a compressed air supply valve that offers the energy required to break up the polymeric solution into microdroplets. When the air valve is opened, the device disperses the polymeric solution by shearing action provided by a high-velocity air stream (around 500 l/h). The nozzle is located 30 cm (distance to n-heptane surface) over a container with n-heptan. The outlet flow is positioned perpendicular to the surface of the coagulation bath. Thus, the microdroplets impact directly on the n-heptane surface.

A photosensitive polymeric solution (10 wt % of poly(styrene-comaleimide-5-(furan-2-ylmethylene)-2,2-dimethyl-1,3-dioxane-4,6-dione) in perfume oil is prepared in a dark bottle to ensure that the photosensitive moieties are in the extended, conjugated form and then poured into the nozzle bulk just before microcapsule production to avoid contact with atmospheric air, which can induce solvent evaporation. The coagulation bath is kept at a temperature of from 0-25° C. to prevent n-heptane evaporation, and it is stirred to prevent aggregation using a magnetic stirrer set at 100 rpm. After precipitation, the photosensitive microcapsules are filtrated, dried in a desiccator, and stored in a dark bottle.

Example 2-6

Examples 2-6 can be made according to the procedure of Example 1, except that the compositions are different (see Table 4). The amount of reagents used depends on the ratio between the styrene and maleic anhydride groups of the poly(styrene-co-maleic anhydride). The amounts of N-methylethylenediamine and Amberlyst® 15 are calculated based on the amount of maleic anhydride groups available for modification with the photosensitive moieties.

TABLE 4

| | Styrene:maleic anhydride in the poly(styrene-co-maleic anhydride) | N-methyl-ethylenediamine (g) | Amberlyst ® 15 (g) |
|---|---|---|---|
| EXAMPLE 2 | 89:11 | 0.45 | 0.94 |
| EXAMPLE 3 | 86:14 | 0.60 | 0.95 |

TABLE 4-continued

| | Styrene:maleic anhydride in the poly(styrene-co-maleic anhydride) | N-methyl-ethylenediamine (g) | Amberlyst ® 15 (g) |
|---|---|---|---|
| EXAMPLE 4 | 80:20 | 0.91 | 0.97 |
| EXAMPLE 5 | 67:33 | 1.22 | 1.02 |
| EXAMPLE 6 | 50:50 | 1.85 | 1.09 |

Example 7

Example 7 can be made according to the procedure of Example 1, except 2.67 g of 5-((furan-2-yl)methylene)-dihydro-1,2,2,3-tetramethylpyrimidine-4,6(1H,5H)-dione is used in place of 2.39 g of 5-(furan-2-ylmethylene)-2,2-dimethyl-1,3-dioxane-4,6-dione.

Example 8

Example 8 can be made according to the procedure of Example 1, except 2.41 g of 2-((furan-2-yl)methylene)-2H-indene-1,3-dione is used in place of 2.39 g of 5-(furan-2-ylmethylene)-2,2-dimethyl-1,3-dioxane-4,6-dione.

Example 9

Example 9 can be made according to the procedure of Example 2, except 1.27 g of 2-((furan-2-yl)methylene)-2H-indene-1,3-dione is used in place of 2.39 g of 5-(furan-2-ylmethylene)-2,2-dimethyl-1,3-dioxane-4,6-dione.

Example 10

Example 10 can be made according to the procedure of Example 6, except 8.61 g of (1,3-bis(4-chlorophenyl)-5-((furan-2-yl)methylene)-dihydro-2,2-dimethylpyrimidine-4,6(1H,5H)-dione is used in place of 2.39 g of 5-(furan-2-ylmethylene)-2,2-dimethyl-1,3-dioxane-4,6-dione.

Example 11

Example 11 can be made according to the procedure of Example 9, except 2.52 g of 5-((furan-2-yl)methylene)-dihydro-2,2-dimethyl-1,3-dioctylpyrimidine-4,6(1H,5H)-dione is used in place of 1.27 g of 2-((furan-2-yl)methylene)-2H-indene-1,3-dione.

Example 12

An acrylate monomer, 2-(tert-butyl((1E,3Z)-5-(2,2-dimethyl-4,6-dioxo-1,3-dioxan-5-ylidene)-4-hydroxypenta-1,3-dien-1-yl)amino)ethyl methacrylate, having the formula:

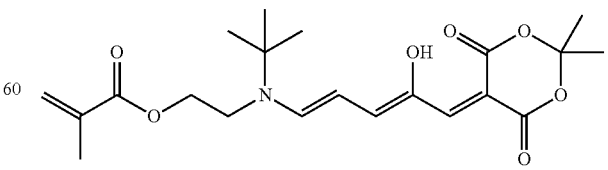

can be made according to the following procedure.

1.711 gram (g) of 5-(furan-2-ylmethylene)-2,2-dimethyl-1,3-dioxane-4,6-dione (Sigma Aldrich) is placed in 100 mL two-necked round bottom flask and is dissolved in 15 mL of tetrahydrofuran (THF) by magnetic stirrer (300 rpm). 1.426 grams of 2-(tert-Butylamino)ethyl methacrylate (Sigma Aldrich) is dissolved in 10 mL of THF and then is added to 5-(furan-2-ylmethylene)-2,2-dimethyl-1,3-dioxane-4,6-dione solution. The mixture is stirred (300 rpm) at 25° C. for 1 hour. During the course of the reaction, change in color can be observed from yellow to dark red. At the completion of the reaction the mixture is cooled to 5° C. for 30 min. As obtained, solution is precipitated by its addition into 150 mL of cold n-heptane. Then, it is centrifuged at 5° C. and 9000 rpm for 30 min. The supernatant is rejected and the obtained solid is dissolved in trichloromethane and washed 10 times with cold water. The organic layer is dried over MgSO$_4$, filtered, and the solvent is removed by rotary evaporation to give 1.670 grams of 2-(tert-butyl((1E,3Z)-5-(2,2-dimethyl-4,6-dioxo-1,3-dioxan-5-ylidene)-4-hydroxypenta-1,3-dien-1-yl)amino)ethyl methacrylate. The obtained product is further purified by chromatographic column using as solid filler silica gel 40-60-microns diameter (CAS 7631-86-9, Acros Organics) and as mobile phase ethyl acetate. Purification is controlled by Thin Layer Chromatography using ethyl acetate as eluent.

Example 13

An acrylate monomer, 5-((2Z,4E)-2-hydroxy-5-(methyl (5-methyl-4-oxohex-5-en-1-yl)amino)penta-2,4-dien-1-ylidene)-2,2-dimethyl-1,3-dioxane-4,6-dione, having the formula:

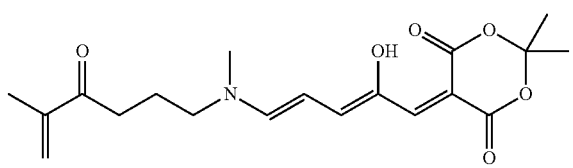 [SMILES: C=C(C)C(=O)CCCN(C)/C=C/C=C(\O)C=C1C(=O)OC(C)(C)OC1=O]

can be made according to the procedure of Example 12, except 1.087 g of 2-methyl-6-(methylamino)hex-1-en-3-one is used in place of 1.426 g of 2-(tert-butylamino)ethyl methacrylate.

Example 14

An acrylate monomer, 5-((2Z,4E)-2-hydroxy-5-(methyl (3-methyl-2-oxobut-3-en-1-yl)amino)penta-2,4-dien-1-ylidene)-2,2-dimethyl-1,3-dioxane-4,6-dione, having the formula:

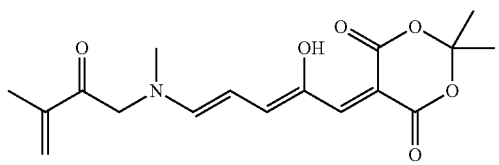 [SMILES: C=C(C)C(=O)CN(C)/C=C/C=C(\O)C=C1C(=O)OC(C)(C)OC1=O]

can be made according to the procedure of Example 12, except 0.871 g of 3-methyl-1-(methylamino)but-3-en-2-one is used in place of 1.426 g of 2-(tert-butylamino)ethyl methacrylate.

Example 15

An acrylate monomer, 5-((2Z,4E)-5-(cyclopropyl(4-methyl-3-oxopent-4-en-1-yl)amino)-2-hydroxypenta-2,4-dien-1-ylidene)-2,2-dimethyl-1,3-dioxane-4,6-dione, having the formula:

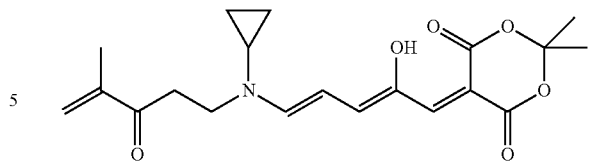

can be made according to the procedure of Example 12, except 1.179 g of 5-(cyclopropylamino)-2-methylpent-1-en-3-one is used in place of 1.426 g of 2-(tert-butylamino)ethyl methacrylate.

Example 16

An acrylate monomer, 5-((2Z,4E)-2-hydroxy-5-(4-(4-methyl-3-oxopent-4-en-1-yl)piperidin-1-yl)penta-2,4-dien-1-ylidene)-2,2-dimethyl-1,3-dioxane-4,6-dione, having the formula:

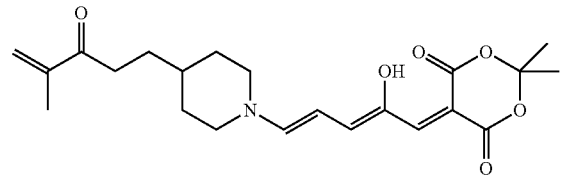 [SMILES: C=C(C)C(=O)CCC1CCN(/C=C/C=C(\O)C=C2C(=O)OC(C)(C)OC2=O)CC1]

can be made according to the procedure of Example 12, except 1.395 g of 2-methyl-5-(piperidin-4-yl)pent-1-en-3-one is used in place of 1.426 g of 2-(tert-butylamino)ethyl methacrylate.

Example 17

An acrylate monomer, 2-(tert-butyl((1E,3Z)-4-hydroxy-5-(1,2,2,3-tetramethyl-4,6-dioxotetrahydropyrimidin-5(2H)-ylidene)penta-1,3-dien-1-yl)amino)ethyl methacrylate, having the formula:

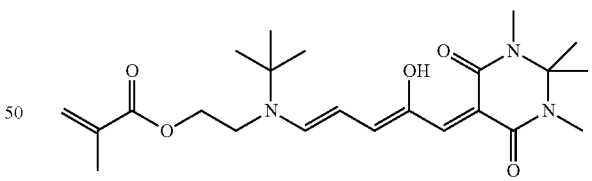

can be made according to the procedure of Example 12, except 1.911 g of 5-((furan-2-yl)methylene)-dihydro-1,2,2,3-tetramethylpyrimidine-4,6(1H,5H)-dione is used in place of 1.711 g of 5-(furan-2-ylmethylene)-2,2-dimethyl-1,3-dioxane-4,6-dione.

Example 18

An acrylate monomer, 2-(tert-butyl((1E,3Z)-5-(1,3-dibutyl-2,2-dimethyl-4,6-dioxotetrahydropyrimidin-5(2H)-ylidene)-4-hydroxypenta-1,3-dien-1-yl)amino)ethyl methacrylate, having the formula:

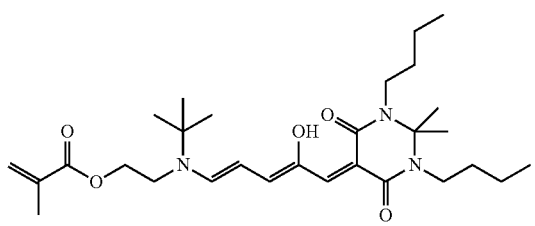 [SMILES: C=C(C)C(=O)OCCN(/C=C/C=C(\O)C=C1C(=O)N(CCCC)C(C)(C)N(CCCC)C1=O)C(C)(C)C]

can be made according to the procedure of Example 12, except 2.559 g of 1,3-dibutyl-5-((furan-2-yl)methylene)-dihydro-2,2-dimethylpyrimidine-4,6(1H,5H)-dione is used in place of 1.711 g of 5-(furan-2-ylmethylene)-2,2-dimethyl-1,3-dioxane-4,6-dione.

Example 19

A hydroxyl monomer, 5-((2Z,4E)-5-((2-ethyl-4-hydroxybutyl)(2-hydroxyethyl)amino)-2-hydroxypenta-2,4-dien-1-ylidene)-2,2-dimethyl-1,3-dioxane-4,6-dione, having the formula

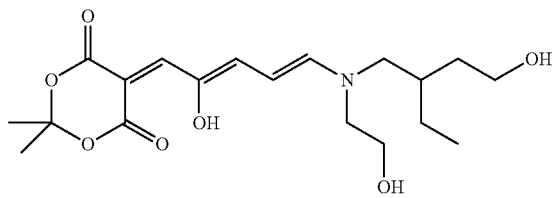 [SMILES: CCC(CCO)CN(/C=C/C=C(\O)C=C1C(=O)OC(C)(C)OC1=O)CCO]

can be made according to the procedure of Example 12, except 1.24 g of 3-((2-hydroxyethylamino)methyl)pentan-1-ol is used in place of 1.426 g of 2-(tert-butylamino)ethyl methacrylate.

Example 20

A hydroxyl monomer, 5-((2Z,4E)-5-(bis(2-hydroxyethyl)amino)-2-hydroxypenta-2,4-dien-1-ylidene)-2,2-dimethyl-1,3-dioxane-4,6-dione, having the formula

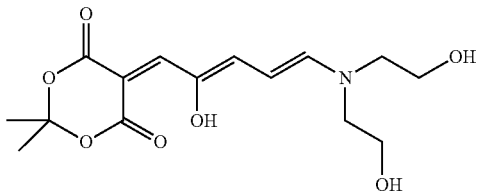 [SMILES: CC1(C)OC(=O)C(=C/C(O)=C/C=C/N(CCO)CCO)C(=O)O1]

can be made according to the procedure of Example 12, except 0.81 g of bis(2-hydroxyethyl)amine is used in place of 1.426 g of 2-(tert-butylamino)ethyl methacrylate.

Example 21

Photosensitive capsules can be prepared utilizing the acrylate monomer of Example 12 according to the following procedure, which includes three steps: (i) preparation of a dispersed phase and a continuous phase, (ii) emulsification, and (iii) polymerization to form the photosensitive microcapsules.

Preparation of the dispersed phase is as follows. 0.284 grams of DASA-acrylate monomer produced in example 12 are added to 71.81 grams of a perfume composition and mixed with a magnetic stirrer at 300 rpm. Then, 0.234 grams of 2-Carboxyethyl acrylate are added followed by 11.23 grams CN975 (Sartomer). The composition is mixed for 30 minutes at 45° C. Then, the composition is cooled to room temperature and 1 gram of 2,2'-Azobis(2,4-dimethylvaleronitrile), 0.23 grams of 2,2'-Azobis(2-methylbutyronitrile) and 35.87 grams isopropyl myristate are sequentially added under continuous stirring.

Separately, a continuous phase is prepared as follows. 3.6 grams of Selvol 540 (Sekisui) are added to 174.9 grams of demineralized water and heated to 80° C. mixing with a magnetic stirrer at 450 rpm till complete dissolution. The solution is cooled down to room temperature and then 0.67 grams 4,4'-Azobis(4-cyanovaleric acid) and 0.79 grams of a 16% caustic soda aqueous solution and mixed for 15 minutes.

The emulsification step is as follows. The dispersed phase is emulsified in the continuous phase using a Silverson L5 homogenizer with an emulsification head at 2500 rpm for 5 min to form an emulsion.

The emulsion is transferred to a reactor equipped with an overhead mixer and a cooler to avoid evaporation during the polymerization and encapsulation steps. Encapsulation is performed by increasing gradually the temperature in several steps: first 15 minutes at 40° C., secondly temperature is increased to 60° C. for 75 min, thirdly temperature is increased to 75° C. for 270 minutes, fourthly temperature is increased to 90° C. for 480 minutes and finally the temperature is lowered to 20° C. for the addition of 0.2 grams acticide MBS2255 and 0.9 grams xanthan gum.

Example 22: Composite Crosslinked DASA Capsules

In order to obtain composite crosslinked capsules, a first solution is prepared by dissolving 0.16 grams of Polyvinyl alcohol (Mowiol®18-88, Mw~130,000 available from Fluka) in 16 mL of demineralized water at 80° C. and 500 rpm. Then, a second solution is prepared by dissolving 0.785 grams of poly(styrene-co-maleic anhydride) containing a styrene maleic anhydride molar ratio 2:1 (SMA2000 available from Total Petrochemicals & Refining USA, Inc., Houston, Tex., USA) and 0.041 grams of photosensitive polymer of Example 3 (containing 86% polystyrene and 14% maleimide-5-(furan-2-ylmethylene)-2,2-dimethyl-1,3-dioxane-4,6-dione moieties) in 6.97 grams of a perfume at 25° C. A third solution is then prepared by dissolving 0.034 grams of 1,4-diaminobutane (Aldrich) and 0.068 grams of sodium bicarbonate (Aldrich) in 7.5 mL demi-water containing 0.075 grams of Polyvinyl alcohol (Mowiol® 18-88, Mw~130,000 available from Fluka). Then, a first composition is prepared by emulsifying the second solution into the first solution at 720 rpm for 30 minutes at 25° C. using an IKA RW20 mixer. Then, the third solution is added drop wise into the dispersion for 10 minutes and encapsulation is achieved by mixing this second composition at 150 rpm for 24 h at 25° C. to form perfume composite capsules.

Example 23

Photosensitive capsules can be prepared utilizing the acrylate monomer of Example 12 according to the following procedure, which includes three steps: (i) preparation of a dispersed phase and a continuous phase, (ii) emulsification, and (iii) polymerization to form the photosensitive microcapsules.

Preparation of the dispersed phase is as follows. 0.065 grams of DASA-acrylate monomer of Example 12 are added to 2 grams of a perfume composition and dispersed using an ultrasound bath (J. P. Selecta S.A., 50/60 Hz, 110 W) for 15 minutes. Then, 3.7 grams chloroform are added and mixed with a magnetic stirrer at 300 rpm for 2 minutes or till complete dissolution of the monomer. Then, 0.025 grams of 2-Carboxyethyl acrylate are added followed by 0.437 grams CN975 (Sartomer). The composition is mixed for 5 minutes at 25° C. Then, 0.215 grams of 2,2'-Azobis(2,4-dimethyl-valeronitrile) and 0.023 grams of 2,2'-Azobis(2-methylbutyronitrile) are added under continuous stirring.

Separately, a continuous phase is prepared as follows. 0.122 grams 4,4'-Azobis(4-cyanovaleric acid) and 0.194 grams of a 16% caustic soda aqueous solution are added to 26.06 grams of a 2% Selvol 540 (Sekisui) aqueous solution and then and mixed for 15 minutes with a magnetic stirrer at 300 rpm.

The emulsification step is as follows. The dispersed phase is emulsified in the continuous phase using a magnetic stirrer at 1000 rpm for 5 min to form an emulsion.

The emulsion is further encapsulated by increasing gradually the temperature in several steps: first 15 minutes at 45° C., secondly temperature is increased to 60° C. for 45 min, thirdly temperature is increased to 75° C. for 75 minutes, fourthly temperature is increased to 90° C. for 150 minutes and finally the temperature is lowered to 20° C. for the characterization and use of the capsules' slurry.

200 μL of the slurry are spread in a 1 cm×5 cm filter paper and introduced in a transparent vial (Headspace crimp vials, ND20 with septum cap from VWR). This operation is repeated 6 times, so 3 vials are exposed to white light and 3 vials are kept in the darkness covered with aluminum folia. After 48 hours, there is a visible difference among samples: the samples maintained in the darkness are pink and the samples exposed to the light discolored to almost white showing the isomerization of the shell comprising DASA moiety. Then, 5 mL hexane are added with a syringe through the septum and the vial containing the slurry spread in the filter paper is mixed gently by hand for 30 seconds. Then, 100 μL of a tonalid solution (0.2 grams tonalid in 25 mL hexane) are added. Then, sample is analyzed by Gas Chromatography (GC).

Two main components of the perfume composition are analyzed, iso bornyl acetate and verdox. This analysis shows a higher release of these perfume components in presence of light:

| % measured by GC | Average after exposure to light (%) | Average in the darkness (%) |
| --- | --- | --- |
| Iso bornyl acetate | 8.27 ± 0.29 | 7.49 ± 0.25 |
| Verdox | 8.08 ± 0.11 | 7.19 ± 0.29 |

Example 24

Liquid laundry detergent composition having a pH of 8 and comprising capsules of the present invention is prepared as follows. First, a liquid laundry detergent formulation is prepared having following composition in Example 24:

| Ingredient | Example 24 (% wt) |
| --- | --- |
| $C_{12-14}$ alkyl ethoxy 3 sulphate | 4 |
| $C_{11-16}$ Alkylbenzene sulphonic acid | 10.4 |
| $C_{14-15}$ alkyl ethoxylation 7 | 4 |
| C12/14 AMINE OXIDE | 0.5 |
| Sodium hydroxide | 3.1 |
| Citric Acid | 2.8 |
| Sodium cumene sulfonate | 1.72 |
| NaCW-B ase | 0.51 |
| Ethanol | 0.4 |
| $C_{12-18}$ Fatty acid | 1.7 |
| Alkoxylated grease cleaning polymer[1] | 1.3 |
| Soil Suspending Alkoxylated Polyalkylemine Polymer[2] | 0.6 |
| Enzymes | up to 1 |
| hydrogenated castor oil | 0.3 |
| Minors (Stabilizers, preservatives, antifoam, dye, brightener, buffers . . . ) | up to 2 |
| Water | balance to 95 |

[1]PG617 or PG640 (BASF, Germany)
[2]600 g/mol molecular weight polyethylenimine core with 24 ethoxylate groups per —NH and 16 propoxylate groups per —NH. Available from BASF (Ludwigshafen, Germany)

Then, capsules from Examples 21, 22, or 23, are added to the liquid laundry detergent formulation of Example 24, and mixed with an overhead mixer at 350 rpm, to prepare Examples 24A-24C containing capsules of the present invention:

| Ingredient | Example 24A | Example 24B % wt | Example 24C |
| --- | --- | --- | --- |
| Liquid laundry detergent formulation of Example 24 | 95 | 95 | 95 |
| Capsules of Example 21 (equivalent to 0.4% perfume) | 1.63 | — | |
| Capsules of Example 22 (equivalent to 0.1% perfume) | — | 0.45 | |
| Capsules of Example 23 (equivalent to 0.25% perfume) | | | 4.1 |
| Water | | balance to 100 | |

The photosensitivity of the capsules in the formulation of Example 24B are analyzed as follows. 1 drop of Example 24B is deposited into a cavity well microscope slide (ref. 1341 from Globe Scientific) and capped with a cover glass. This sample is prepared twice, one is left in the darkness and the other one is exposed to 254 nm light (UV-GL55, 733-2365, from VWR) for 140 min at a distance of 20 cm. After this time both samples are checked under light microscope (such as Axioscope from Zeiss). It is observed that the capsules of the sample slide left in the darkness are still intact while the capsules of the sample slide exposed to light are broken and the perfume is released.

Example 25

The following Examples 25A and 25B are skin care compositions containing capsules of the present invention:

| Ingredient | Example 25A | Example 25B % wt |
| --- | --- | --- |
| Glycerin | 7 | |
| Linear alcohols | 3.3 | |
| Isohexadecane | 3 | |
| Vitamine E Acetate | 0.5 | |
| Sepigel 305 | 0.5 | |
| Silicone | 2 | |

-continued

| Ingredient | Example 25A | Example 25B |
|---|---|---|
| | % wt | |
| Niacinamide | | 5 |
| Capsules of Example 21 (equivalent to 0.1% perfume) | 0.4 | — |
| Capsules of Example 22 (equivalent to 0.05% perfume) | — | 0.23 |
| Minors (stabilizers, buffers, preservative ...) | | <3 |
| Demineralized water | | balance to 100 |

Values disclosed herein as ends of ranges are not to be understood as being strictly limited to the exact numerical values recited. Instead, unless otherwise specified, each numerical range is intended to mean both the recited values and any integers within the range. For example, a range disclosed as "1 to 10" is intended to mean "1, 2, 3, 4, 5, 6, 7, 8, 9, and 10."

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A photosensitive microcapsule comprising
   a. a core material comprising a benefit agent; and
   b. a shell comprising a photosensitive polymer;
      wherein the photosensitive polymer comprises a photosensitive moiety comprising a structure selected from the group consisting of

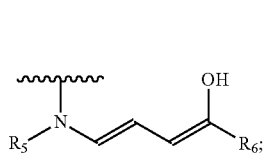 , 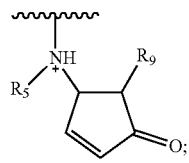

and combinations thereof;
   wherein $R_5$ is selected from alkyl, substituted alkyl, alkoxy, substituted alkoxy, carboxy, carboxyl, substituted carboxyl, aryl, substituted aryl, or a carbon atom of a polymer backbone;
   wherein $R_6$ and $R_9$ comprise a 1,3 dione moiety;
   wherein the photosensitive moiety is incorporated in a monomer that is polymerized to form the photosensitive polymer, wherein the monomer is selected from the group consisting of: 2-(tert-butyl((1E,3Z)-5-(2,2-dimethyl-4,6-dioxo-1,3-dioxan-5-ylidene)-4-hydroxypenta-1,3-dien-1-yl)amino)ethyl methacrylate; 5-((2Z,4E)-2-hydroxy-5-(methyl(3-methyl-2-oxobut-3-en-1-yl)amino)penta-2,4-dien-1-ylidene)-2,2-dimethyl-1,3-dioxane-4,6-dione; 5-(2Z,4E)-5-(cyclopropyl(4-methyl-3-oxopent-4-en-1-yl)amino)-2-hydroxypenta-2,4-dien-1-ylidene)-2,2-dimethyl-1,3-dioxane-4,6-dione; 5-((2Z,4E)-2-hydroxy-5-(4-(4-methyl-3-oxopent-4-en-1-yl)piperidin-1-yl)penta-2,4-dien-1-ylidene)-2,2-dimethyl-1,3-dioxane-4,6-dione; 2-(tert-butyl((1E,3Z)-4-hydroxy-5-(1,2,2,3-tetramethyl-4,6-dioxotetrahydropyrimidin-5(2H)-ylidene)penta-1,3-dien-1-yl)amino)ethyl methacrylate; 2-(tert-butyl((1E,3Z)-5-(1,3-dibutyl-2,2-dimethyl-4,6-dioxotetrahydropyrimidin-5(2H)-ylidene)-4-hydroxypenta-1,3-dien-1-yl)amino)ethyl methacrylate; 5-(2Z,4E)-5-((2-ethyl-4-hydroxybutyl)(2-hydroxyethyl)amino)-2-hydroxypenta-2,4-dien-1-ylidene)-2,2-dimethyl-1,3-dioxane-4,6-dione; 5-((2Z,4E)-5-(bis(2-hydroxyethyl)amino)-2-hydroxypenta-2,4-dien-1-ylidene)-2,2-dimethyl-1,3-dioxane-4,6-dione; 4,4'-(((1E,3Z)-5-(2,2-dimethyl-4,6-dioxo-1,3-dioxan-5-ylidene)-4-hydroxypenta-1,3-dien-1-yl)azanediyl) dibutanal, and mixtures thereof.

2. The photosensitive microcapsule of claim 1 wherein $R_6$ is selected from the group consisting of

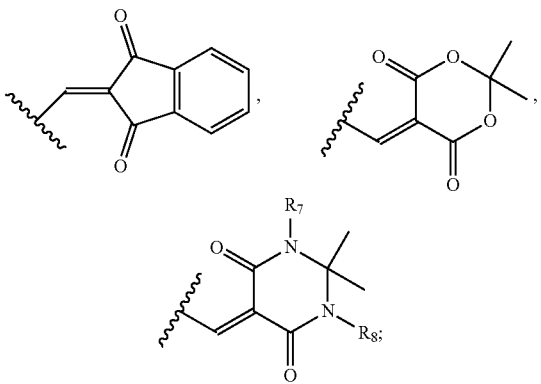

wherein $R_7$ and $R_8$ are independently selected from the group consisting of H, alkyl, substituted alkyl, aryl, and substituted aryl.

3. The photosensitive microcapsule of claim 1 wherein $R_9$ is selected from the group consisting of

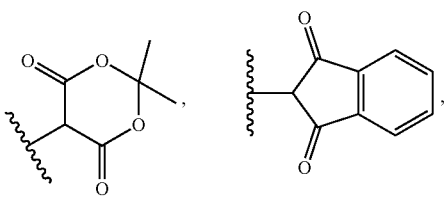

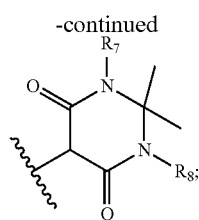

wherein $R_7$ and $R_8$ are independently selected from the group consisting of H, alkyl, substituted alkyl, aryl, and substituted aryl.

4. The photosensitive microcapsule of claim 1, wherein the photosensitive polymer comprises the following structure

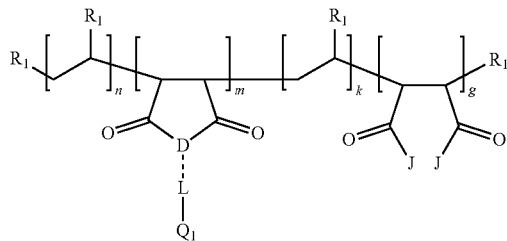

wherein m+g>0 and (n+k)/(m+g)≥1;
wherein $R_1$ is selected from H, alkyl, substituted alkyl, alkoxy, substituted alkoxy, aryl, substituted aryl, carboxy, carboxyl, substituted carboxyl, or nitrile;
wherein D=N or 0;
wherein for D=N: L is a linker group containing at least one carbon atom and $Q_1$ is the photosensitive moiety;
wherein J=OH, $OR_{12}$, $NH_2$, $NHR_{12}$, or $NR_{12}R_{13}$;
wherein $R_{12}$ and $R_{13}$ are independently selected from alkyl, substituted alkyl, alkoxy, aryl, or $L-Q_1$.

5. The photosensitive microcapsule of claim 4, wherein $R_1$ is an aryl group.

6. The photosensitive microcapsule of claim 4, wherein L comprises the following formula

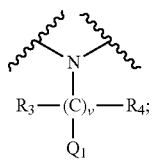

wherein v is an integer from 1-20; and
wherein $R_3$ and $R_4$ can be independently selected from the group consisting of H, alkyl, substituted alkyl, allyl, substituted allyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, alloxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, sulfonyl, substituted sulfonyl, C1-C20 cyclic, substituted C1-C20 cyclic, heterocyclic, and substituted heterocyclic groups.

7. The photosensitive microcapsule of claim 4, wherein the photosensitive polymer comprises from about 1% to about 25% of cross-linked functional groups.

8. The photosensitive microcapsule of claim 1, wherein the photosensitive polymer comprises the following structure:

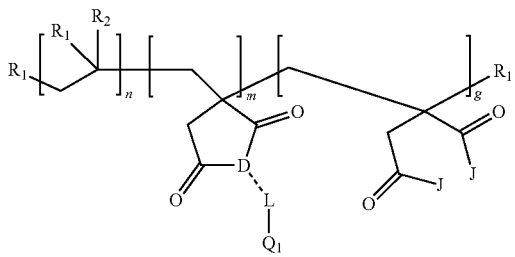

wherein m+g>0 and n≥0;
wherein $R_1$ is selected from H, alkyl, substituted alkyl, alkoxy, substituted alkoxy, aryl, substituted aryl, carboxy, carboxyl, substituted carboxyl, or nitrile;
wherein $R_2$ is selected from H or $CH_3$;
wherein D=N or 0;
wherein for D=N: L is a linker group containing at least one carbon atom and $Q_1$ is the photosensitive moiety;
wherein J=OH, $OR_{12}$, $NH_2$, $NHR_{12}$, or $NR_{12}R_{13}$;
wherein $R_{12}$ and $R_{13}$ are independently selected from alkyl, substituted alkyl, alkoxy, aryl, or $L-Q_1$.

9. The photosensitive microcapsule of claim 1, wherein the photosensitive polymer comprises the following structure:

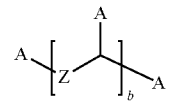

wherein $Z=Q_1$ or $CH_2$;
wherein $A=R_1$ or $A=Q_1$ when $Z=CH_2$;
wherein $Q_1$ is the photosensitive moiety;
wherein $R_1$ is selected from H, alkyl, substituted alkyl, alkoxy, substituted alkoxy, aryl, substituted aryl, carboxy, carboxyl, substituted carboxyl, nitrile, siloxy alkyl, or silo alkyl.

10. The photosensitive microcapsule of claim 1 comprising from about 1 wt % to about 95 wt % of the photosensitive moiety.

11. The photosensitive microcapsule of claim 1 wherein the benefit agent is selected from the group consisting of a perfume, a biocontrol agent, a dye, a silicone, a flavor, a skin care agent, a sunscreen agent, a sensate, a pharmaceutically active ingredient, and combinations thereof.

12. A method of releasing a core material from the photosensitive microcapsule of claim 1 comprising: exposing the photosensitive microcapsule to an electromagnetic radiation field selected from the group consisting of infrared radiation, visible light, ultraviolet radiation, and mixtures thereof.

13. The method of claim 12 wherein the electromagnetic radiation field comprises a wavelength of from about 200 nm to about 1000 nm.

14. A composition comprising one or more photosensitive microcapsules according to claim 1 and an adjunct ingredient.

15. The composition of claim 14, comprising, based on total composition weight, from about 0.1% to about 25% of photosensitive microcapsules.

* * * * *